(12) United States Patent
Ueda et al.

(10) Patent No.: US 11,464,782 B2
(45) Date of Patent: Oct. 11, 2022

(54) METHOD OF TREATING PAIN OR INTERSTITIAL CYSTITIS USING INDOLE COMPOUND

(71) Applicant: Japan Tobacco Inc., Tokyo (JP)

(72) Inventors: Yoshifumi Ueda, Takatsuki (JP); Mutsuyoshi Matsushita, Takatsuki (JP); Yoshihiro Kitagawa, Takatsuki (JP); Akira Matsuo, Takatsuki (JP); Tatsuya Maekawa, Takatsuki (JP); Sotaro Takigawa, Tokyo (JP); Hiromitsu Watanabe, Tokyo (JP); Naoki Miyagawa, Tokyo (JP); Yuji Hamada, Takatsuki (JP); Tetsuya Hondo, Princeton, NJ (US)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 17/056,936

(22) PCT Filed: May 24, 2019

(86) PCT No.: PCT/JP2019/021649
§ 371 (c)(1),
(2) Date: Nov. 19, 2020

(87) PCT Pub. No.: WO2019/225768
PCT Pub. Date: Nov. 28, 2019

(65) Prior Publication Data
US 2021/0205320 A1    Jul. 8, 2021

Related U.S. Application Data

(60) Provisional application No. 62/835,675, filed on Apr. 18, 2019.

(30) Foreign Application Priority Data

May 25, 2018 (JP) .............................. JP2018100671
Dec. 28, 2018 (JP) .............................. JP2018246392

(51) Int. Cl.
*A61K 31/5355* (2006.01)
*A61P 13/10* (2006.01)
*A61P 25/02* (2006.01)
*A61P 29/00* (2006.01)
*A61K 9/00* (2006.01)

(52) U.S. Cl.
CPC ........ *A61K 31/5355* (2013.01); *A61K 9/0053* (2013.01); *A61P 13/10* (2018.01); *A61P 25/02* (2018.01)

(58) Field of Classification Search
CPC ...... A61K 31/5355; A61P 13/10; A61P 23/00; A61P 25/02
See application file for complete search history.

(56) References Cited

U.S. PATENT DOCUMENTS

| 8,299,070 | B2 | 10/2012 | Inoue et al. |
| 11,104,667 | B2 | 8/2021 | Inoue et al. |
| 2011/0306599 | A1 | 12/2011 | Inoue et al. |
| 2013/0116240 | A1 | 5/2013 | Inoue et al. |
| 2017/0253577 | A1 | 9/2017 | Inoue et al. |
| 2017/0267662 | A1 | 9/2017 | Inoue et al. |
| 2018/0362506 | A1 | 12/2018 | Inoue et al. |
| 2020/0255408 | A1 | 8/2020 | Inoue et al. |
| 2021/0236502 | A1 | 8/2021 | Ueda et al. |
| 2021/0236503 | A1 | 8/2021 | Ueda et al. |
| 2021/0284627 | A1 | 9/2021 | Inoue et al. |

FOREIGN PATENT DOCUMENTS

| CN | 104628657 A | 5/2015 |
| EP | 3165525 A | 5/2017 |
| WO | WO2011065402 A | 6/2011 |
| WO | WO2016002918 A | 1/2016 |
| WO | WO2019225740 A | 11/2019 |
| WO | WO2019225741 A | 11/2019 |

OTHER PUBLICATIONS

PCT International Search Report and Written Opinion in International Appln. No. PCT/JP2019/021649, dated Nov. 28, 2019, 9 pages.

*Primary Examiner* — Theodore R. Howell
(74) *Attorney, Agent, or Firm* — Fish & Richardson P.C.

(57) ABSTRACT

Provided is a therapeutic or prophylactic agent for pain or interstitial cystitis comprising N-[2-(6,6-dimethyl-4,5,6,7-tetrahydro-H-indazol-3-yl)-1H-indol-6-yl]-N-methyl-(2S)-2-(morpholin-4-yl)propanamide or a pharmaceutically acceptable salt thereof.

121 Claims, 12 Drawing Sheets

Mean values + standard deviations, n = 8 except for the Normal group (n = 6), **; $p < 0.01$ vs. the Normal group (Student's t test), §, §§; $p < 0.05$, $p < 0.01$ vs. the Vehicle group (Steel test)

Data are shown as mean and standard deviation (n=8); ** p<0.01 vs. Sham group (Student's t test); ## p<0.01 vs. Vehicle group (Dunnett's test).

Data are shown as mean and standard deviation (n=8); ‡ p<0.01 vs. Sham group (Welch's test); ## p<0.01 vs. Vehicle group (Dunnett's test).

METHOD OF TREATING PAIN OR INTERSTITIAL CYSTITIS USING INDOLE COMPOUND

CROSS-REFERENCE TO RELATED APPLICATIONS

This application is the U.S. National Stage of International Application No. PCT/JP2019/021649, filed on May 24, 2019, which claims priority to Japanese Appl. No. Appl. No. 2018-100671, filed May 25, 2018, Japanese Appl. No. Appl. No. 2018-246392, filed Dec. 28, 2018, and U.S. Provisional Appl. No. 62/835,675, filed Apr. 18, 2019. The contents of the prior applications are incorporated by reference herein in their entirety.

TECHNICAL FIELD

The present invention pertains to medicinal use of N-[2-(6,6-dimethyl-4,5,6,7-tetrahydro-1H-indazol-3-yl)-1H-indol-6-yl]-N-methyl-(2S)-2-(morpholin-4-yl)propanamide or a pharmaceutically acceptable salt thereof as a therapeutic agent or prophylactic agent for pain or interstitial cystitis.

BACKGROUND

Physiologically speaking, pain signals play a key role as a warning system for an organism, but "pathological" pain adversely affects an organism and decreases the quality of life. Opioids (narcotic analgesics such as morphine), non-steroid anti-inflammatory drugs (NSAIDs), acetaminophen and other agents such as duloxetine and pregabalin are used for the therapy of pain. However, pain management by current anti-pain agents is not sufficient. In addition, opioids, while considered to be the most efficacious of anti-pain agents, are associated with a growing epidemic of abuse, dependence and overdose in many countries.

Interstitial cystitis is a disease that is associated with non-specific chronic inflammation of the bladder and presents symptoms such as frequent urination, increased desire to urinate, urinary urgency, and/or bladder pain, and it produces marked deterioration of quality of life. Interstitial cystitis associated with pain or a condition where interstitial cystitis is suspected is sometimes included among painful bladder syndrome, bladder pain syndrome, or chronic pelvic pain syndrome. The three conditions of (1) the presence of lower urinary tract symptoms such as frequent urination, hypersensitive bladder, and/or bladder pain, (2) the ability to confirm endoscopically lesions of the bladder resulting from Hunner's ulcers and/or bleeding after bladder dilatation, and (3) the fact that other disorders such as infection, malignant tumor, or urinary calculus are excludable is one example of a diagnostic standard for interstitial cystitis. Interstitial cystitis is broadly classified as Hunner-type, presenting with Hunner's ulcers, or non-Hunner-type, presenting with no Hunner's ulcers.

SUMMARY

The invention is based, at least in part, on the inventors' discovery that N-[2-(6,6-dimethyl-4,5,6,7-tetrahydro-1H-indazol-3-yl)-1H-indol-6-yl]-N-methyl-(2S)-2-(morpholin-4-yl)propanamide (referred to herein as "Compound A") reduces sensitivity to pain. Based on this discovery, Compound A or a pharmaceutically acceptable salt thereof can be used as an effective medication to treat or prevent pain.

The invention is also based, at least in part, on the inventors' discovery that Compound A reduces the severity of interstitial cystitis. Based on this discovery, Compound A or a pharmaceutically acceptable salt thereof can be used as an effective medication to treat or prevent interstitial cystitis.

In one aspect, the invention features a method of treating or preventing pain in a human subject in need thereof by administering to the human subject a therapeutically effective amount of a compound represented by the following chemical structural formula:

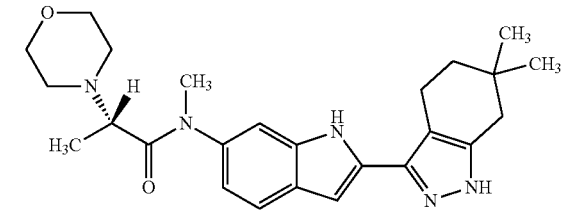 [SMILES: C[C@@H](C(=O)N(C)c1ccc2cc(-c3n[nH]c4c3CCC(C)(C)C4)[nH]c2c1)N1CCOCC1]

or a pharmaceutically acceptable salt thereof.

The present invention also includes a pharmaceutical composition for the treatment or prophylaxis of pain that contains Compound A or a pharmaceutically acceptable salt thereof.

The present invention also includes the use of Compound A or a pharmaceutically acceptable salt thereof for the production of a therapeutic agent or prophylactic agent for pain.

The present invention also includes Compound A or a pharmaceutically acceptable salt thereof for use in the treatment or prophylaxis of pain.

The present invention also includes a therapeutic agent or prophylactic agent for pain comprising Compound A or a pharmaceutically acceptable salt thereof.

In some embodiments, the pain is neuropathic pain.
In some embodiments, the pain is nociceptive pain.
In some embodiments, the pain is mixed pain.
In some embodiments, the pain is inflammatory pain, musculoskeletal pain, or cancer pain.
In some embodiments, the pain is pain of osteoarthritis.
In some embodiments, the pain is low back pain.
In some embodiments, the pain is pain of interstitial cystitis.
In some embodiments, the pain is pain of diabetic peripheral neuropathy.
In some embodiments, the pain is pain of rheumatoid arthritis.
In some embodiments, the pain is not pain of rheumatoid arthritis.
In some embodiments, the pain is not pain of interstitial cystitis.
In some embodiments, the pain is not pain of rheumatoid arthritis or interstitial cystitis.
In some embodiments, the pain is painful bladder syndrome, bladder pain syndrome, or chronic pelvic pain syndrome.
In some embodiments, the pain is associated with inflammation, pancreatitis, kidney stones, a headache, dysmenorrhea, musculoskeletal pain, a sprain, visceral pain, an ovarian cyst, prostatitis, cystitis, inflammatory bowel disease, post-surgical pain, a migraine, trigeminal neuralgia, burns, wounds, trauma, post-herpetic neuralgia, a musculoskeletal disease, ankylosing spondylitis, a periarticular pathology, cancer, bone metastases, HIV, myocardial infarction, fracture, gout, joints, sciatica, a sickle cell crisis, endometriosis, fibromyalgia, incisional pain, erythromelalgia, malignant melanoma, Sjogren's syndrome, asthma, chronic abacterial prostatitis, uterine fibroids, vulvodynia, phantom limb pain, root avulsions, diabetic neuropathic pain, painful traumatic mononeuropathy, painful polyneuropathy, a central pain syndrome, repetitive motion pain, myofascial pain, perioperative pain, chronic pain, angina, primary hyperalgesia, secondary hyperalgesia, primary allodynia, secondary allodynia, osteoporosis, irritable bowel syndrome, pulpitis, a contusion of the skin, tendonitis, colic, appendicitis, peptic ulcer disease, bladder distension, a bruise, peritendinitis, frozen shoulder, spinal compression fracture, spinal stricture, spinal stenosis, spinal disc herniation, cervicobranchial syndrome, spinal burst fracture, pain after exodontia, acute arterial occlusion, or erythromelalgia.

In some embodiments, the compound or pharmaceutically acceptable salt thereof is administered orally.

In some embodiments, the compound or pharmaceutically acceptable salt thereof is administered once daily.

In some embodiments, the compound or pharmaceutically acceptable salt thereof is administered orally once daily.

In some embodiments, the pain is moderate pain.

In some embodiments, the pain is moderate to severe pain.

In some embodiments, the pain is severe pain.

In some embodiments, the pharmaceutically acceptable salt is a monohydrochloride.

In some embodiments, the compound or pharmaceutically acceptable salt thereof is administered orally and the pain is moderate pain.

In some embodiments, the compound or pharmaceutically acceptable salt thereof is administered orally and the pain is moderate to severe pain.

In some embodiments, the compound or pharmaceutically acceptable salt thereof is administered orally and the pain is severe pain.

In some embodiments, a monohydrochloride of the compound is administered orally and the pain is moderate pain.

In some embodiments, a monohydrochloride of the compound is administered orally and the pain is moderate to severe pain.

In some embodiments, a monohydrochloride of the compound is administered orally and the pain is severe pain.

In some embodiments, the compound or pharmaceutically acceptable salt thereof is administered orally at a dose equivalent to no less than 50 mg of the compound.

In some embodiments, the compound or pharmaceutically acceptable salt thereof is administered orally at a dose equivalent to about 50-400 mg of the compound.

In some embodiments, the compound or pharmaceutically acceptable salt thereof is administered orally at a dose equivalent to about 50-200 mg of the compound.

In some embodiments, the compound or pharmaceutically acceptable salt thereof is administered orally at a dose equivalent to about 75-200 mg of the compound.

In some embodiments, the compound or pharmaceutically acceptable salt thereof is administered orally at a dose equivalent to about 75-150 mg of the compound.

In some embodiments, the compound or pharmaceutically acceptable salt thereof is administered orally at a dose equivalent to about 75 mg, about 100 mg, about 125 mg, or about 150 mg of the compound.

In some embodiments, the compound or pharmaceutically acceptable salt thereof is administered once daily (e.g., at a dose equivalent of about 50-200 mg of the compound) and results in mean trough concentration ($C_{trough}$) of the compound of about 100 ng/mL to about 550 ng/mL for at least about 12 weeks.

In some embodiments, the compound or pharmaceutically acceptable salt thereof is administered once daily (e.g., at a dose equivalent of about 50 mg of the compound) and results in mean trough concentration ($C_{trough}$) of the compound of about 100 ng/mL to about 150 ng/mL for at least about 12 weeks.

In some embodiments, the compound or pharmaceutically acceptable salt thereof is administered once daily (e.g., at a dose equivalent of about 100 mg of the compound) and results in mean trough concentration ($C_{trough}$) of the compound of about 150 ng/mL to about 250 ng/mL for at least about 12 weeks.

In some embodiments, the compound or pharmaceutically acceptable salt thereof is administered once daily (e.g., at a dose equivalent of about 150 mg of the compound) and results in mean trough concentration ($C_{trough}$) of the compound of about 250 ng/mL to about 350 ng/mL for at least about 12 weeks.

In some embodiments, the compound or pharmaceutically acceptable salt thereof is administered once daily (e.g., at a dose equivalent of about 200 mg of the compound) and results in mean trough concentration ($C_{trough}$) of the compound of about 300 ng/mL to about 550 ng/mL for at least about 12 weeks.

In another aspect, the invention features a method of treating or preventing interstitial cystitis in a human subject in need thereof by administering to the human subject a therapeutically effective amount of a compound represented by the following chemical structural formula:

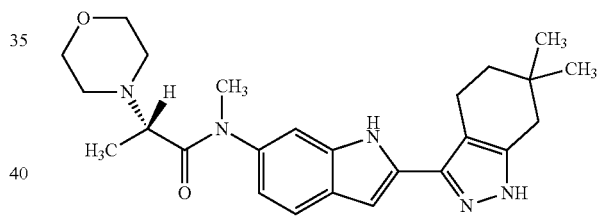

or a pharmaceutically acceptable salt thereof.

The invention also features a method of treating or preventing overactive bladder or cystitis in a urinary tract infection in a human subject in need thereof by administering to the human subject a therapeutically effective amount of a compound represented by the following chemical structural formula:

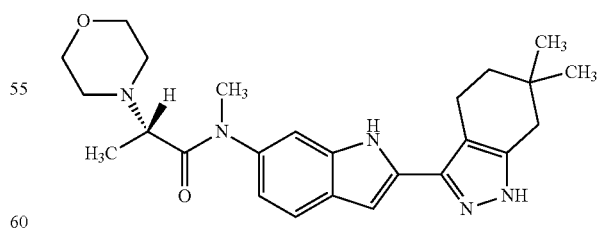

or a pharmaceutically acceptable salt thereof.

The present invention also includes a pharmaceutical composition for the treatment or prophylaxis of interstitial cystitis (or overactive bladder or cystitis in a urinary tract infection) that contains Compound A or a pharmaceutically acceptable salt thereof.

The present invention also includes the use of Compound A or a pharmaceutically acceptable salt thereof for the production of a therapeutic agent or prophylactic agent for interstitial cystitis (or overactive bladder or cystitis in a urinary tract infection).

The present invention also includes Compound A or a pharmaceutically acceptable salt thereof for use in the treatment or prophylaxis of interstitial cystitis (or overactive bladder or cystitis in a urinary tract infection).

The present invention also includes a therapeutic agent or prophylactic agent for interstitial cystitis (or overactive bladder or cystitis in a urinary tract infection) comprising Compound A or a pharmaceutically acceptable salt thereof.

In some embodiments, the interstitial cystitis is characterized by at least one symptom selected from the group consisting of frequent urination, nocturia, urinary urgency, increased desire to urinate, hypersensitive bladder, bladder discomfort, bladder pain, and inflammation of the bladder.

In some embodiments, the interstitial cystitis is Hunner-type interstitial cystitis or non-Hunner-type interstitial cystitis.

In some embodiments, the compound or pharmaceutically acceptable salt thereof is administered orally.

In some embodiments, the compound or pharmaceutically acceptable salt thereof is administered once daily.

In some embodiments, the compound or pharmaceutically acceptable salt thereof is administered orally once daily.

In some embodiments, the pharmaceutically acceptable salt is a monohydrochloride.

In some embodiments, a monohydrochloride of the compound is administered orally.

In some embodiments, a monohydrochloride of the compound is administered orally once daily.

In some embodiments, the compound or pharmaceutically acceptable salt thereof is administered orally at a dose equivalent to no less than 50 mg of the compound.

In some embodiments, the compound or pharmaceutically acceptable salt thereof is administered orally at a dose equivalent to about 50-400 mg of the compound. For example, the compound or pharmaceutically acceptable salt thereof is in some embodiments administered orally at a dose equivalent to about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, or about 400 mg of the compound.

BRIEF DESCRIPTION OF THE DRAWINGS

FIG. 2A), at 2 weeks (FIG. 2B), and at 12 weeks (FIG. 2C).

DETAILED DESCRIPTION

Compound A and Pharmaceutically Acceptable Salts

Figure 1:
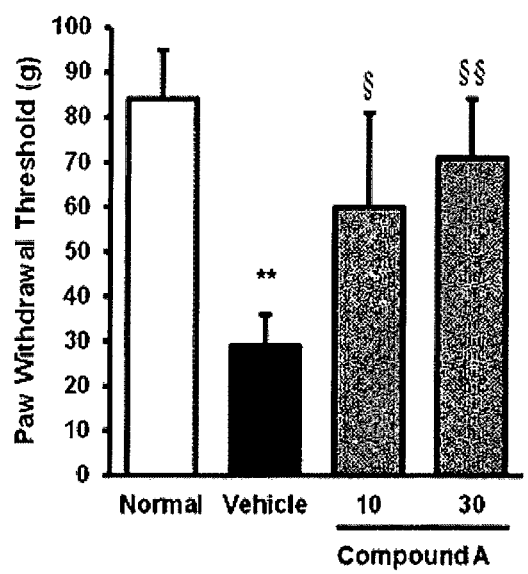
FIG. 1 shows the pain thresholds of CIA model rats to which a vehicle, or a monohydrochloride of Compound A in an amount equivalent to 10 mg/kg or 30 mg/kg of Compound A was orally administered, and normal rats to which a vehicle was orally administered.

"Compound A" is N-[2-(6,6-dimethyl-4,5,6,7-tetrahydro-1H-indazol-3-yl)-1H-indol-6-yl]-N-methyl-(2S)-2-(morpholin-4-yl)propanamide, and is represented by the following chemical structural formula:

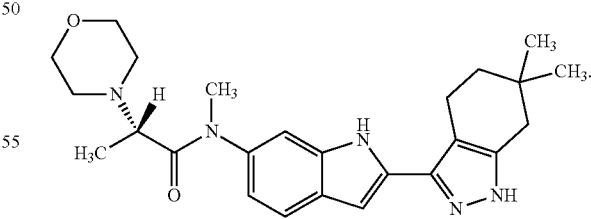

Any salt known in the technical field is acceptable as a "pharmaceutically acceptable salt" as long as it is not accompanied by excessive toxicity. Specifically, salts with inorganic acids, salts with organic acids, salts with inorganic bases, and salts with organic bases can be given as examples. Various forms of pharmaceutically acceptable salt are well known in the field and are described in the references below, for example:

(a) Berge et al, J. Pharm. Sci., 66, p 1-19 (1977),
(b) Stahl et al, "Handbook of Pharmaceutical Salts: Properties, Selection, and Use" (Wiley-VCH, Weinheim, Germany, 2002), and
(c) Paulekuhn et al, J. Med. Chem., 50, p 6665-6672 (2007).

It is possible to obtain the respective pharmaceutically acceptable salts of Compound A by reacting Compound A with an inorganic acid, an organic acid, an inorganic base, or an organic base according to a method known per se. It is also acceptable for a pharmaceutically acceptable salt of Compound A to be formed of an acid or a base having half the number of molecules in Compound A, the same number of molecules as in Compound A, or at least twice the number of molecules of Compound A.

Salts with hydrofluoric acid, hydrochloric acid, hydrobromic acid, hydriodic acid, nitric acid, phosphoric acid, or sulfuric acid are given as examples of salts with inorganic acids.

Salts with acetic acid, adipic acid, alginic acid, 4-aminosalicylic acid, anhydromethylene citric acid, benzoic acid, benzenesulfonic acid, calcium edetate, camphoric acid, camphor-10-sulfonic acid, carbonic acid, citric acid, edetic acid, 1,2-ethanedisulfonic acid, dodecyl sulfate, ethane sulfonic acid, fumaric acid, glucoheptonate, gluconic acid, glucuronic acid, glycollylarsanilate, hexylresorcinate, hydroxynaphthoic acid, 2-hydroxy-1-ethanesulfonic acid, lactic acid, lactobionic acid, malic acid, maleic acid, mandelic acid, methanesulfonic acid, methylsulfuric acid, methyl nitrate, methylenebis (salicylic acid), galactaric acid, naphthalene-2-sulfonic acid, 2-naphthoic acid, 1,5-naphthalenedisulfonic acid, oleic acid, oxalic acid, pamoic acid, pantothenic acid, pectic acid, picric acid, propionic acid, polygalacturonic acid, salicylic acid, stearic acid, succinic acid, tannic acid, tartaric acid, teoclate, thiocyanic acid, trifluoroacetic acid, p-toluenesulfonic acid, undecanoic acid, asparagine acid, or glutamic acid are given as examples of salts with organic acids.

Salts with lithium, sodium, potassium, magnesium, calcium, barium, aluminum, zinc, bismuth, or ammonium are given as examples of salts with inorganic bases.

Salts with arecoline, betaine, choline, clemizole, ethylenediamine, N-methylglucamine, N-benzylphenethylamine, tris(hydroxymethyl)methylamine, arginine, or lysine are given as examples of salts with organic bases.

Preferred embodiments of a "pharmaceutically acceptable salt" are as follows.

Salts with hydrochloric acid, nitric acid, sulfuric acid, phosphoric acid, or hydrobromic acid are given as examples of salts with inorganic acids.

Salts with oxalic acid, maleic acid, citric acid, fumaric acid, lactic acid, mallic acid, succinic acid, tartaric acid, acetic acid, trifluoroacetic acid, benzoic acid, glucuronic acid, oleic acid, pamoic acid, methanesulfonic acid, benzenesulfonic acid, p-toluenesulfonic acid, or 2-hydroxy-1-ethanesulfonic acid are given as examples of salts with organic acids.

Salts with sodium, potassium, calcium, magnesium, or zinc are given as examples of salts with inorganic bases.

Salts with tris(hydroxymethyl)methylamine, N-methylglucamine, or lysine are given as examples of salts with organic bases.

A preferable pharmaceutically acceptable salt of Compound A among these is a monohydrochloride of Compound A represented by the following chemical structural formula:

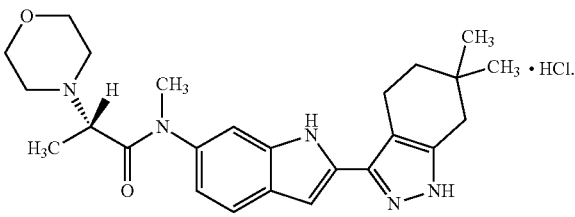 [SMILES: C[C@@H](C(=O)N(C)c1ccc2cc(-c3n[nH]c4c3CCC(C)(C)C4)[nH]c2c1)N1CCOCC1]

Compound A and the pharmaceutically acceptable salts thereof can be produced using a known method, a method described in WO 2011/065402 or WO 2016/002918, for example.

Compound A or the pharmaceutically acceptable salts thereof may exist as a solvate.

A "solvate" has a molecule of a solvent coordinated to Compound A or a pharmaceutically acceptable salt thereof, and this encompasses a hydrate. A pharmaceutically acceptable solvate is preferable as a solvate, and examples include a hydrate, an ethanol solvate, or a dimethyl sulfoxide solvate of Compound A or a pharmaceutically acceptable salt thereof.

Specifically, a hemihydrate, monohydrate, dihydrate, or mono(ethanol)solvate of Compound A, or a monohydrate of a sodium salt or a 2/3(ethanol)solvate of a dihydrochloride of Compound A can be given as examples. These solvates can be obtained according to known methods.

Compound A or a pharmaceutically acceptable salt thereof, each of which has been substantially purified, is preferable as Compound A or a pharmaceutically acceptable salt thereof. More preferably, Compound A or a pharmaceutically acceptable salt thereof has been purified to a purity of at least 80%.

The therapeutic agent or prophylactic agent for pain or interstitial cystitis of the present invention is produced, for example, according to a known method in the technical field of medicinal preparations by mixing Compound A or a pharmaceutically acceptable salt thereof with a suitable amount of at least one kind of pharmaceutically acceptable carrier or the like as appropriate. The amount of Compound A or a pharmaceutically acceptable salt thereof in said preparation differs according to the dosage form, dose, and the like, but is, for example, 0.1 to 100 wt % of the entire preparation.

The therapeutic agent or prophylactic agent of the present invention can be administered orally or parenterally. Oral administration or parenteral administration such as intravenous, intramuscular, subcutaneous, percutaneous, local, or rectal administration can be given as examples of dosage forms. Tablets, capsules, granules, powders, troches, syrups, emulsions, suspensions, and the like can be given as examples of dosage forms that are appropriate for oral administration, and external preparations, suppositories, injections, eye drops, eye ointments, patches, gels, implants, nasal preparations, or pulmonary preparations can be given as examples of dosage forms that are appropriate for parenteral administration. These can be prepared according to known methods in the technical field of medicinal preparations.

Examples of a "pharmaceutically acceptable carrier" include various organic or inorganic carrier substances conventionally used as formulation materials, and examples include excipients, disintegrants, binders, fluidizers, lubricants, and the like for solid preparations; solvents, solubilizing agents, suspending agents, isotonicity agents, buffering agents, soothing agents, and the like for liquid preparations; and bases, emulsifiers, humectants, stabilizers, labilizing agents, dispersants, plasticizers, pH regulators, absorption promoters, gelling agents, antiseptics, fillers, solvents, solubilizers, suspending agents, and the like for semisolid preparations. It is also acceptable to use additives such as preservatives, antioxidants, colorants, sweetening agents, and the like as necessary.

Examples of an "excipient" include lactose, sucrose, D-mannitol, D-sorbitol, cornstarch, dextrin, microcrystalline cellulose, crystalline cellulose, carmellose, carmellose calcium, sodium carboxymethyl starch, low-substituted hydroxypropylcellulose, gum arabic, and the like.

Examples of a "disintegrant" include carmellose, carmellose calcium, carmellose sodium, sodium carboxymethyl starch, croscarmellose sodium, crospovidone, low-substituted hydroxypropylcellulose, hydroxypropylmethylcellulose, crystalline cellulose, and the like.

Examples of a "binder" include hydroxypropylcellulose, hydroxypropylmethylcellulose, povidone, crystalline cellulose, sucrose, dextrin, starch, gelatin, carmellose sodium, gum arabic, and the like.

Examples of a "fluidizer" include light anhydrous silicic acid, magnesium stearate, and the like.

Examples of a "lubricant" include magnesium stearate, calcium stearate, talc, and the like.

Examples of a "solvent" include purified water, ethanol, propylene glycol, macrogol, sesame oil, corn oil, olive oil, and the like.

Examples of a "solubilizing agent" include propylene glycol, D-mannitol, benzyl benzoate, ethanol, triethanolamine, sodium carbonate, sodium citrate, and the like.

Examples of a "suspending agent" include benzalkonium chloride, carmellose, hydroxypropylcellulose, propylene glycol, povidone, methylcellulose, glycerol monostearate, and the like.

Examples of an "isotonic agent" include glucose, D-sorbitol, sodium chloride, D-mannitol, and the like.

Examples of a "buffering agent" include sodium hydrogenphosphate, sodium acetate, sodium carbonate, sodium citrate, and the like.

Examples of a "soothing agent" include benzyl alcohol and the like.

Examples of a "base" include water, vegetable oils (olive oil, corn oil, peanut oil, sesame oil, castor oil, and the like), lower alcohols (ethanol, propanol, propylene glycol, 1,3-butylene glycol, phenol, and the like), higher fatty acids and esters thereof, waxes, higher alcohols, polyhydric alcohols, hydrocarbons (white petrolatum, liquid paraffin, paraffin, and the like), hydrophilic petrolatum, purified lanolin, absorptive ointments, hydrous lanolin, hydrophilic ointments, starches, pullulan, gum arabic, tragacanth gum, gelatins, dextran, cellulose derivatives (methyl cellulose, carboxymethyl cellulose, hydroxyethyl cellulose, hydroxypropyl cellulose, and the like), synthetic polymers (carboxyvinyl polymer, sodium polyacrylate, polyvinyl alcohol, polyvinyl pyrrolidone, and the like), propylene glycol, macrogol (Macrogol 200-600 and the like), and a combination of two or more kinds of these.

Examples of a "preservative" include ethyl parahydroxybenzoate, chlorobutanol, benzyl alcohol, sodium dehydroacetate, sorbic acid, and the like.

Examples of an "antioxidant" include sodium sulfite, ascorbic acid, and the like.

Examples of a "colorant" include food colorings (such as Food Red No. 2 or No. 3, or Food Yellow No. 4 or No. 5), β-carotene, and the like.

Examples of a "sweetening agent" include saccharine sodium, dipotassium glycyrrhizinate, aspartame, and the like.

Formulation examples of the present invention include the following formulations. The present invention is not, however, limited by these formulation examples.

Formulation Example 1: Production of a capsule

| | |
|---|---|
| 1) Monohydrochloride of Compound A | 30 mg |
| 2) Microcrystalline cellulose | 10 mg |
| 3) Lactose | 19 mg |
| 4) Magnesium stearate | 1 mg |

1), 2), 3), and 4) are mixed and filled in a gelatin capsule.

Formulation Example 2: Production of a tablet

| | |
|---|---|
| 1) Monohydrochloride of Compound A | 10 g |
| 2) Lactose | 50 g |
| 3) Corn starch | 15 g |
| 4) Carmellose calcium | 44 g |
| 5) Magnesium stearate | 1 g |

The total amounts of 1), 2), and 3) and 30 g of 4) are kneaded with water, vacuum dried, and sieved. The sieved powder is mixed with 14 g of 4) and 1 g of 5), and the mixture is punched by means of a tableting machine. In this way, 1,000 tablets each containing 10 mg of the monohydrochloride of Compound A per tablet are obtained.

Treatment or Prevention of Pain

Compound A or a pharmaceutically acceptable salt thereof can be used as an active ingredient of a therapeutic agent or prophylactic agent for pain.

In this specification, "therapy" includes the improvement of pain, the prevention or delay of an increase in severity, the maintenance of remission, the prevention of exacerbation, and moreover, the prevention of relapse.

In this specification, "prophylaxis" signifies the inhibition of the onset of pain.

Compound A or a pharmaceutically acceptable salt thereof can be used in combination (hereinafter also referred to as "concomitantly") with one or multiple other drugs (hereinafter also referred to as a "concomitant drug") using a common practice employed in the medical field.

Examples of a concomitant drug include analgesics and adjuvant analgesics. Analgesics include opioid receptor agonists, opioid receptor partial agonists, NSAIDs, COX-2 inhibitors, ion channel modulators, centrally acting agents, agents for neuropathic pain, agents for cancer pain, and other analgesics. Adjuvant analgesics include antidepressants, antiepileptic agents, antiarrhythmic agents, N-methyl-D-aspartate antagonists, centrally acting muscle relaxants, corticosteroids, antianxiety agents, bone modifying agents, antihistamine agents, neuroleptic agents, and other adjuvant analgesics.

Examples of opioid receptor agonists include Morphine, Oxycodone, Pethidine, Methadone, Levorphanol, Oxymorphone, Fentanyl, Pentazocine, Tramadol, Hydromorphone, Fentanyl, Remifentanil, Tapentadol, Hydrocodone, Sufentanil, Benzhydrocodone, Oxycodegol Codeine, and Dihydrocodeine.

Examples of opioid receptor partial agonists include Dextromoramide, Buprenorphine, Butorphanol, Nalbuphine, Meptazinol, Eptazocine, and Dinalbuphine.

Examples of NSAIDs include Acetylsalicylic acid, Paracetamol, Indometacin, Mefenamic acid, Ibuprofen, Naproxen, Diclofenac, Fenoprofen, Fenbufen, Ketoprofen, Sulindac, Flurbiprofen, Diflunisal, Piroxicam, Acemetacin, Meclofenamate, Propacetamol, Ketorolac, Aceclofenac, Zaltoprofen, Mofezolac, Dexketoprofen, Lornoxicam, Meloxicam, and Pelubiprofen.

Examples of COX-2 inhibitors include Rofecoxib, Celecoxib, Parecoxib, and Lumiracoxib.

Examples of ion channel modulators include Ziconotide, Bupivacaine, and Priralfinamide.

Examples of centrally acting agents include Nefopam and Flupirtine.

Examples of agents for neuropathic pain include Carbamazepine, Lidocaine, Clonidine, Gabapentin, Duloxetine, Pregabalin, Capsaicin, and Mirogabalin.

Examples of agents for cancer pain include Calcitonin, Clodronate, Pamidronate, Strontium, and Lexidronam.

Examples of other analgesics include Eptinezumab, Lasmiditan, Ubrogepant, Atogepant, Oliceridine, Cebranopadol, Fasinumab, Lucerastat, Neridronic acid, Relugolix, Rimegepant, Tanezumab, Zoledronic acid, and Zucapsaicin.

Examples of antidepressants include Amitriptyline, Amoxapine, Nortriptyline, Duloxetine, Paroxetine, Fluvoxamine, Imipramine, Desipramine, Trazodone, Bupropion, Doxepine, and Venlafaxine.

Examples of antiepileptic agents include Pregabalin, Gabapentin, Valproic acid, Phenytoin, Clonazepam, and Carbamazepine.

Examples of antiarrhythmic agents include Mexiletine and Lidocain.

Examples of N-methyl-D-aspartate antagonists include Ketamine.

Examples of centrally acting muscle relaxants Baclofen, Orphenadrine, Carisoprodol, Methocarbamol, Chlorzoxazone, and Cyclobenzaprine.

Examples of corticosteroids include Betamethasone and Dexamethasone.

Examples of antianxiety agents include Diazepam and Lorazepam.

Examples of bone modifying agents include Zoledronic acid, Denosumab, Calcitonin, and Strontium 89.

Examples of antihistamine agents include Hyroxyzine and Diphenhydramine.

Examples of neuroleptic agents include Methotrimeprazine and Fluphenazine.

Examples of other adjuvant analgesics include Octreotide, Scopolamine, Glycopyrrolate, Clonidine, and Capsaicin.

The timing of administration of a drug comprising Compound A or a pharmaceutically acceptable salt thereof and a concomitant drug is not limited, it is acceptable to administer these to an administration subject as a combination drug, and it is also acceptable to administer the two formulations either simultaneously or at a fixed interval. Furthermore, it is also acceptable to use the therapeutic agent or prophylactic agent of the present invention and a concomitant drug as a medication that is characterized in that the medication is a kit comprising said agent and concomitant drug. The dosage of a concomitant drug is acceptable as long as it is based on a dosage used in clinical practice, and the dosage can be appropriately selected according to the administration subject, disease, symptoms, dosage form, administration route, administration time, combination, and so on. The dosage form of a concomitant drug is not particularly limited, and is acceptable as long as a drug comprising Compound A or a pharmaceutically acceptable salt thereof are combined with the concomitant drug.

Examples of one embodiment of the present invention include a method for the treatment or prophylaxis of pain that comprises administering to a human a therapeutically effective amount of Compound A or a pharmaceutically acceptable salt thereof.

In this specification, an "effective amount" signifies, for example, the amount of a medication or drug that elicits a biological or medical response in a tissue, system, or human. Furthermore, a "therapeutically effective amount" signifies an arbitrary amount that either produces a treatment, cure, prophylaxis, or improvement where pain or a side effect is improved in comparison with a corresponding subject that has not received such an amount.

The dosage of the therapeutic agent or prophylactic agent of the present invention differs according to the administration subject, disease, symptoms, dosage form, administration route, and so on. For example, the daily dose for oral administration to an adult patient (body weight: approximately 60 kg) is generally within the range of 0.1 mg to 1 g, and preferably 10 mg to 800 mg, when calculated using Compound A as the active ingredient, and this amount can be administered in one to several portions per day either before a meal, after a meal, or during a meal. It is also acceptable to administer the agent once or multiple times per day, for example, as needed if pain has developed. The duration of administration is not particularly limited.

Examples of dose ranges for Compound A or a pharmaceutically acceptable salt thereof include orally administering a dose equivalent to no less than 50 mg of the compound, e.g., a dose equivalent to about 50-400 mg of the compound, a dose equivalent to about 50-200 mg of the compound, a dose equivalent to about 75-200 mg of the compound, or a dose equivalent to about 75-150 mg of the compound.

Examples of dose ranges for monohydrochloride of Compound A include orally administering a dose equivalent to no less than 50 mg of the compound, e.g., a dose equivalent to about 50-400 mg of the compound, a dose equivalent to about 50-200 mg of the compound, a dose equivalent to about 75-200 mg of the compound, or a dose equivalent to about 75-150 mg of the compound. Unless otherwise specified, the compound means a free form of the compound.

Examples of doses for Compound A or a pharmaceutically acceptable salt thereof include orally administering at a dose equivalent to about 75 mg, about 100 mg, about 125 mg, or about 150 mg of the compound.

Compound A or a pharmaceutically acceptable salt thereof can be administered once daily to a subject to provide mean trough concentration ($C_{trough}$) of the compound of about 100 ng/mL to about 600 ng/mL for at least about 12 weeks. For example, administration of the dose equivalent of about 50-200 mg of the compound to the human subject once daily can result in mean trough concentration ($C_{trough}$) of the compound of about 100 ng/mL to about 550 ng/mL for at least about 12 weeks. The terms "trough concentration" and "$C_{trough}$" refer to the lowest concentration of Compound A in the plasma of the human subject before the next dose of Compound A, or pharmaceutically acceptable salt thereof, is administered. The mean $C_{trough}$ can be about 120 ng/mL to about 520 ng/mL.

Administration of the dose equivalent of about 50 mg of the compound once daily to the human subject can result in mean trough concentration ($C_{trough}$) of the compound of about 100 ng/mL to about 150 ng/mL for at least about 12 weeks. For example, the mean $C_{trough}$ can be about 120 ng/mL to about 140 ng/mL.

Administration of the dose equivalent of about 100 mg of the compound once daily to the human subject can result in mean trough concentration ($C_{trough}$) of the compound of about 150 ng/mL to about 250 ng/mL for at least about 12 weeks. For example, the mean $C_{trough}$ can be about 180 ng/mL to about 230 ng/mL.

Administration of the dose equivalent of about 150 mg of the compound once daily to the human subject can result in mean trough concentration ($C_{trough}$) of the compound of about 250 ng/mL to about 350 ng/mL for at least about 12 weeks. For example, the mean $C_{trough}$ can be about 270 ng/mL to about 340 ng/mL.

Administration of the dose equivalent of about 200 mg of the compound once daily to the human subject can result in mean trough concentration ($C_{trough}$) of the compound of about 300 ng/mL to about 550 ng/mL for at least about 12 weeks. For example, the mean $C_{trough}$ can be about 350 ng/mL to about 550 ng/mL. For example, the mean $C_{trough}$ can be about 350 ng/mL to about 450 ng/mL.

The Numerical Rating Scale (NRS) can be used to quantify pain and measure progress in pain management. Using a 0-10 scale, NRS scores less than or equal to 5 are generally considered to correspond to mild pain, scores of 6-7 are generally considered to correspond to moderate pain, and scores greater than or equal to 8 are generally considered to correspond to severe pain. As described in the Examples, Compound A was found to reduce pain in subjects having pain greater than or equal to 8 on the NRS scale, indicating that it can be used to treat subjects having severe pain.

The Visual Analogue Scale (VAS) can also be used to quantify pain and measure progress in pain management. The VAS consists of a straight line with the endpoints defining extreme limits such as "no pain" and "worst possible pain." The subject is asked to mark his/her pain level on the line between the two endpoints. The distance between "no pain" and the mark defines the subject's pain.

Examples of one embodiment of the present invention include a pharmaceutical composition for the treatment or prophylaxis of pain that contains Compound A or a pharmaceutically acceptable salt thereof.

Examples of one embodiment of the present invention include the use of Compound A or a pharmaceutically acceptable salt thereof for the production of a therapeutic agent or prophylactic agent for pain.

Examples of one embodiment of the present invention include Compound A or a pharmaceutically acceptable salt thereof for use in the treatment or prophylaxis of pain.

Examples of one embodiment of the present invention include a therapeutic agent or prophylactic agent for pain comprising Compound A or a pharmaceutically acceptable salt thereof.

Treatment or Prevention of Interstitial Cystitis

Compound A or a pharmaceutically acceptable salt thereof can be used as an active ingredient of a therapeutic agent or prophylactic agent for interstitial cystitis. Furthermore, Compound A or a pharmaceutically acceptable salt thereof can be used for the therapy or prophylaxis of symptoms of interstitial cystitis such as frequent urination, nocturia, urinary urgency, increased desire to urinate, hypersensitive bladder, bladder discomfort, bladder pain, and inflammation of the bladder.

Interstitial cystitis is broadly classified as Hunner-type, presenting with Hunner's ulcers, or non-Hunner-type, presenting with no Hunner's ulcers. Compound A or a pharmaceutically acceptable salt thereof can be used as an active ingredient of a therapeutic agent or prophylactic agent for either type of interstitial cystitis.

Compound A or a pharmaceutically acceptable salt thereof can also be used as an active ingredient of a therapeutic agent or prophylactic agent for overactive bladder or cystitis in a urinary tract infection. Overactive bladder and cystitis in a urinary tract infection are diseases that exhibit frequent urination (i.e., pollakiuria), a symptom in common with interstitial cystitis. In some instances, overactive bladder is diagnosed as a disease distinct from interstitial cystitis because of no microscopic finding in the bladder. In some cases, however, the population of overactive bladder subjects may include interstitial cystitis subjects without such microscopic diagnosis.

In this specification, "therapy" includes the improvement of interstitial cystitis (or overactive bladder or cystitis in a urinary tract infection), the prevention or delay of an increase in severity, the maintenance of remission, the prevention of exacerbation, and moreover, the prevention of relapse.

In this specification, "prophylaxis" signifies the inhibition of the onset of interstitial cystitis (or overactive bladder or cystitis in a urinary tract infection).

The therapeutic agent or prophylactic agent of the present invention can be used in combination (hereinafter also referred to as "concomitantly") with one or multiple other drugs (hereinafter also referred to as a "concomitant drug") using a common practice employed in the medical field.

The timing of administration of a drug comprising Compound A or a pharmaceutically acceptable salt thereof and a concomitant drug is not limited, it is acceptable to administer these to an administration subject as a combination drug, and it is also acceptable to administer the two formulations either simultaneously or at a fixed interval. Furthermore, it is also acceptable to use the therapeutic agent or prophylactic agent of the present invention and a concomitant drug as a medication that is characterized in that the medication is a kit comprising said agent and concomitant drug. The dosage of a concomitant drug is acceptable as long as it is based on a dosage used in clinical practice, and the dosage can be appropriately selected according to the administration subject, disease, symptoms, dosage form, administration route, administration time, combination, and so on. The dosage form of a concomitant drug is not particularly limited, and is acceptable as long as a drug comprising Compound A or a pharmaceutically acceptable salt thereof are combined with the concomitant drug. Examples of a concomitant drug include hydroxyzine, amitriptyline, suplatast tosilate, cimetidine, corticosteroids, cyclosporine, antibiotics, and oxybutynin.

Examples of one embodiment of the present invention include a method for the treatment or prophylaxis of interstitial cystitis (or overactive bladder or cystitis in a urinary tract infection) that comprises administering to a human a therapeutically effective amount of Compound A or a pharmaceutically acceptable salt thereof.

In this specification, an "effective amount" signifies, for example, the amount of a medication or drug that elicits a biological or medical response in a tissue, system, or human. Furthermore, a "therapeutically effective amount" signifies an arbitrary amount that either produces a treatment, cure, prophylaxis, or improvement where interstitial cystitis or a side effect is improved in comparison with a corresponding subject that has not received such an amount.

The dosage of the therapeutic agent or prophylactic agent of the present invention differs according to the administration subject, disease, symptoms, dosage form, administration route, and so on. For example, the daily dose for oral administration to an adult patient (body weight: approximately 60 kg) is generally within the range of 0.1 mg to 1 g, and preferably 10 mg to 800 mg, when calculated using Compound A as the active ingredient, and this amount can be administered in one to several portions per day either before a meal, after a meal, or during a meal. It is also acceptable to administer the agent once or multiple times per day, for example, as needed if pain has developed. The duration of administration is not particularly limited.

Examples of dose ranges for Compound A or a pharmaceutically acceptable salt thereof include orally administering a dose equivalent to no less than 50 mg of the compound, e.g., a dose equivalent to about 50-400 mg of the compound, a dose equivalent to about 50-200 mg of the compound, a dose equivalent to about 75-200 mg of the compound, or a dose equivalent to about 75-150 mg of the compound.

Examples of doses for Compound A or a pharmaceutically acceptable salt thereof include orally administering a dose equivalent to about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, or about 400 mg of the compound.

Examples of one embodiment of the present invention include a pharmaceutical composition for the treatment or prophylaxis of interstitial cystitis (or overactive bladder or cystitis in a urinary tract infection) that contains Compound A or a pharmaceutically acceptable salt thereof.

Examples of one embodiment of the present invention include the use of Compound A or a pharmaceutically acceptable salt thereof for the production of a therapeutic agent or prophylactic agent for interstitial cystitis (or overactive bladder or cystitis in a urinary tract infection).

Examples of one embodiment of the present invention include Compound A or a pharmaceutically acceptable salt thereof for use in the treatment or prophylaxis of interstitial cystitis (or overactive bladder or cystitis in a urinary tract infection).

Examples of one embodiment of the present invention include a therapeutic agent or prophylactic agent for interstitial cystitis (or overactive bladder or cystitis in a urinary tract infection) comprising Compound A or a pharmaceutically acceptable salt thereof.

The present invention will be explained below in detail using examples of embodiment, but the present invention is not limited by these examples of embodiment.

The following examples are provided to better illustrate the claimed invention and are not to be interpreted as limiting the scope of the invention. To the extent that specific materials are mentioned, it is merely for purposes of illustration and is not intended to limit the invention. One skilled in the art can develop equivalent means or reactants without the exercise of inventive capacity and without departing from the scope of the invention.

EXAMPLES

Example 1: Analgesic Effect Resulting from the Oral Administration of a Monohydrochloride of Compound A in a Rat Collagen-Induced Arthritis (CIA) Model The analgesic effect of Compound A on hypersensitivity to pain during the onset of arthritis in a rat CIA model was evaluated. Hypersensitivity to pain was evaluated using the paw withdrawal threshold (PWT) in relation to mechanical stimulus using the Randall-Selitto method.

Female LEW/CrlCrlj rats (Charles River Laboratories Japan, Inc.) were used for the experiment. A monohydrochloride of Compound A was dissolved in 0.5% methyl cellulose (MC) to prepare 2 mg/mL and 6 mg/mL solutions of Compound A. Type II collagen derived from joint bovine cartilage (Collagen Research Center) was dissolved in acetic acid to prepare a 2 mg/mL type II collagen solution. Equal volumes of the 2 mg/mL type II collagen solution and incomplete Freund's adjuvant were mixed to prepare a 1 mg/mL type II collagen emulsion.

On Day 1, the type II collagen emulsion was intradermally injected into the animals in the vehicle group, the Compound A 10 mg/kg administration group, and the Compound A 30 mg/kg administration group. On Day 8, the type II collagen emulsion was intradermally injected into the animals in the vehicle group, the Compound A 10 mg/kg administration group, and the Compound A 30 mg/kg administration group. On Days 22 through 28, a 0.5% MC solution was orally administered once per day to the vehicle group at a volume of 5 mL/kg. During the same period 2 mg/mL or 6 mg/mL of a Compound A solution was orally administered once per day to the Compound A 10 mg/kg administration group and the Compound A 30 mg/kg administration group respectively at a volume of 5 mL/kg. On Day 28, the analgesic effect was measured using a Randall-Selitto analgesy-meter (TK-201, UNICOM). The means values and standard deviations of the PWT values for each group were calculated. The results are shown in FIG. 1. Compound A attenuated hyperalgesia in rats with CIA.

Example 2: Effect of Compound A on Nerve Growth Factor (NGF)-Induced Hyperalgesia in Rats Compound A has an inhibitory effect on TrkA, a receptor for NGF. The objective of the present study was to investigate the effects of Compound A on NGF-induced hyperalgesia in rats.

In order to induce a pain-related behavior (withdrawal behavior), NGF was injected into the plantar area of the left hind paw of rats and the thermal latencies/mechanical thresholds were measured. The effects of Compound A on these withdrawal behaviors were investigated.

At 2 days before the injection of NGF, the thermal latencies or mechanical thresholds were measured for acclimation to the experimental environment. On the day before injection of NGF, body weights and values of the thermal latencies or mechanical thresholds were obtained.

50 μL of NGF solution was injected intraplantar to left hind paw of rats. 0.5 μg/site of NGF was selected in the evaluation of thermal stimuli and 1 μg/site was selected in that of mechanical stimuli. A monohydrochloride of Compound A (1, 3, or 10 mg/kg) was administered orally at the same time as the NGF injection.

The latencies to thermal stimuli were measured at 3 and 6 hours after injection of NGF solution, and the thresholds to mechanical stimuli were measured at 1, 3 and 6 hours after injection of NGF solution. The evaluation was performed as a blind test of each group.

The thermal latency was measured using a plantar test apparatus. An infrared heat stimuli was delivered to the plantar area of the hind paw and the time to withdraw the paw from the heat source was recorded automatically as the thermal latency. The measurement was performed 5 times for both hind paws of each animal, the averages of the last 3 values in each hind paw were accounted as the thermal latencies of each animal. The measurement for acclimation was performed only 3 times.

The mechanical threshold was measured using a pressure analgesy-meter. A mechanical stimulus (pressure) increased at a constant rate was added to the hind paw, and the pressure under load until animals withdrew its hind paw or vocalization was recorded as the mechanical threshold (mmHg).

Compound A prevented the decrease in the thermal latencies induced by NGF compared with the vehicle in a dose related manner. See Table 1. Significant effects of Compound A were observed from the dose of 3 mg/kg at 6 hours after NGF injection.

TABLE 1

Effects of Compound A on NGF-induced thermal hyperalgesia in female rats

| | Paw Withdrawal Latency (s) | | | | | |
|---|---|---|---|---|---|---|
| | Right hind paw (uninjected side) | | | Left hind paw (injected side) | | |
| Group | pre | 3 hr | 6 hr | pre | 3 hr | 6 hr |
| Sham | 11.4 ± 2.0 | 10.7 ± 2.0 | 10.4 ± 1.8 | 10.8 ± 1.8 | 10.5 ± 2.0 | 9.7 ± 1.8 |
| Vehicle (0 mg/kg) | 10.5 ± 0.9 | 10.0 ± 1.1 | 11.4 ± 1.8 | 10.9 ± 1.9 | 5.7 ± 1.5** | 5.4 ± 1.5** |
| Compound A•HCl 1 mg/kg | 11.6 ± 1.1 | 10.9 ± 1.4 | 10.8 ± 2.4 | 11.4 ± 1.2 | 10.0 ± 2.6# | 8.7 ± 2.0 |
| Compound A•HCl 3 mg/kg | 11.6 ± 1.5 | 12.3 ± 2.2 | 11.9 ± 1.9 | 11.2 ± 1.9 | 10.3 ± 1.6# | 9.9 ± 1.5# |
| Compound A•HCl 10 mg/kg | 11.9 ± 1.2 | 11.9 ± 2.7 | 11.5 ± 1.2 | 12.0 ± 1.1 | 11.6 ± 2.4# | 11.3 ± 1.4# |

Each value represents the mean ± standard deviation, n = 6.
NGF at a concentration of 0.5 μg/site was injected intraplantar of left hind paw.
**$p < 0.01$ vs. sham (Wilcoxon test)
$p < 0.05$ vs. vehicle (0 mg/kg) (Steel test)

Compound A prevented the decrease in the mechanical thresholds induced by NGF compared with the vehicle in a dose related manner. See Table 2. Significant effects of Compound A were observed from the dose of 3 mg/kg at 6 hours after NGF injection.

TABLE 2

Effects of Compound A on NGF-induced mechanical hyperalgesia in female rats

| | Paw Withdrawal Threshold (mmHg) | | | | | | | |
|---|---|---|---|---|---|---|---|---|
| | Right hind paw (uninjected side) | | | | Left hind paw (injected side) | | | |
| Group | pre | 1 hr | 3 hr | 6 hr | Pre | 1 hr | 3 hr | 6 hr |
| Sham | 137 ± 20 | 128 ± 19 | 128 ± 14 | 138 ± 29 | 135 ± 20 | 136 ± 20 | 131 ± 10 | 134 ± 23 |
| Vehicle (0 mg/kg) | 131 ± 18 | 133 ± 15 | 126 ± 10 | 139 ± 23 | 131 ± 15 | 94 ± 18** | 72 ± 22** | 75 ± 15** |
| Compound A•HCl 1 mg/kg | 132 ± 15 | 134 ± 16 | 135 ± 21 | 133 ± 9 | 126 ± 21 | 107 ± 17 | 104 ± 20 | 90 ± 11 |
| Compound A•HCl 3 mg/kg | 148 ± 25 | 133 ± 19 | 141 ± 10 | 144 ± 23 | 152 ± 26 | 118 ± 17 | 121 ± 21# | 106 ± 11# |
| Compound A•HCl 10 mg/kg | 139 ± 17 | 144 ± 14 | 139 ± 17 | 139 ± 13 | 136 ± 17 | 130 ± 20# | 134 ± 22# | 130 ± 18# |

Each value represents the mean ± standard deviation, n = 6.
NGF at a concentration of 1 μg/site was injected intraplantar of left hind paw.
**$p < 0.01$ vs. sham (Wilcoxon test)
$p < 0.05$ vs. vehicle (Steel test)

Example 3: Pain Evaluation in Rheumatoid Arthritis Human Clinical Trial

Compound A was evaluated in a multicenter, randomized, double-blind, placebo-controlled, parallel-group study in subjects with active rheumatoid arthritis. Subjects were randomized to receive orally placebo or an amount of monohydrochloride Compound A sufficient to provide 50 mg, 100 mg, 150 mg, or 200 mg of free form, once daily for 12 weeks.

Pain was evaluated using a Numerical Rating Scale (NRS) by subjects. The pain NRS represents the severity of their arthritis pain during the past 3 days using an 11-point scale from 0 (no pain) to 10 (maximum pain). An evaluation was made of how much NRS decreased from baseline NRS after drug administration.

Data from EOT (end of treatment), at 2 weeks, and at 12 weeks was obtained. EOT is a measurement point generally used in clinical studies. In a 12-week study, it refers to all analysis at the 12-week time point. However, since some subjects will have discontinued the study midway, the data at the time of discontinuation is treated as the EOT for these subjects (for example, data for week 8 is used as EOT for subjects who discontinued in week 8). 2-week (subjects who completed 2 weeks in full) and 12-week (subjects who completed 12 weeks in full) data are also presented.

Figure 2A:
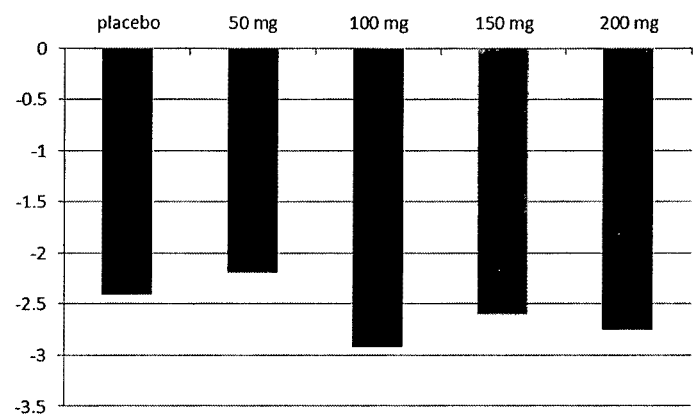
FIGS. 2A-2C are graphs depicting the amount of change from baseline in Numerical Rating Scale (NRS) pain, after treatment with placebo or a monohydrochloride of Compound A, at end of treatment (EOT.
Figure 2B:
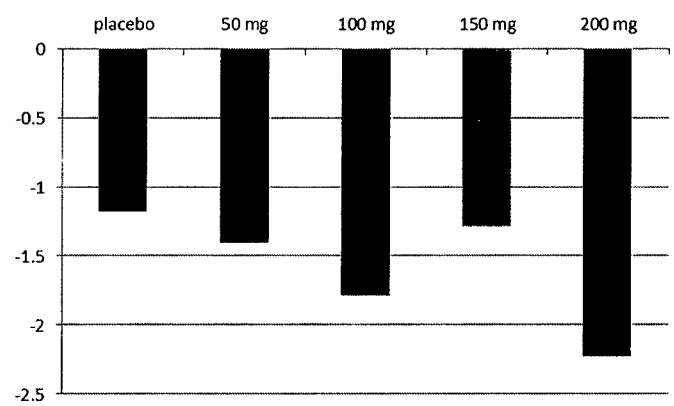
Figure 2C:
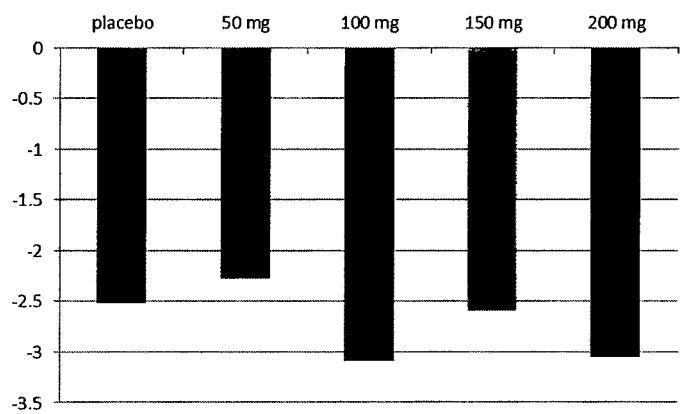

The amounts of change from baseline in NRS pain after treatment with placebo or one of the doses of Compound A are shown in FIG. 2A (at EOT), FIG. 2B (at 2 weeks), and FIG. 2C (at 12 weeks).

Figure 3A:
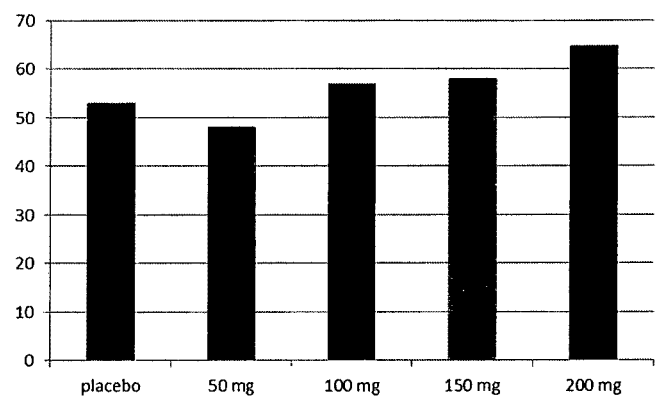
FIGS. 3A-3C are graphs depicting the percentage of patients achieving at least a 30% improvement in pain, after treatment with placebo or a monohydrochloride of Compound A, at EOT (FIG. 3A), at 2 weeks (FIG. 3B), and at 12 weeks (FIG. 3C).
Figure 3B:
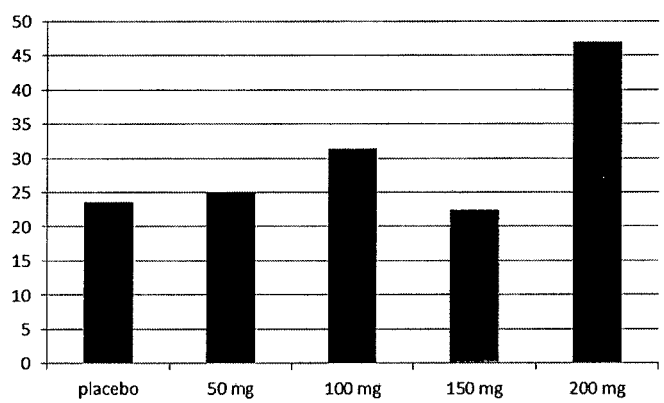
Figure 3C:
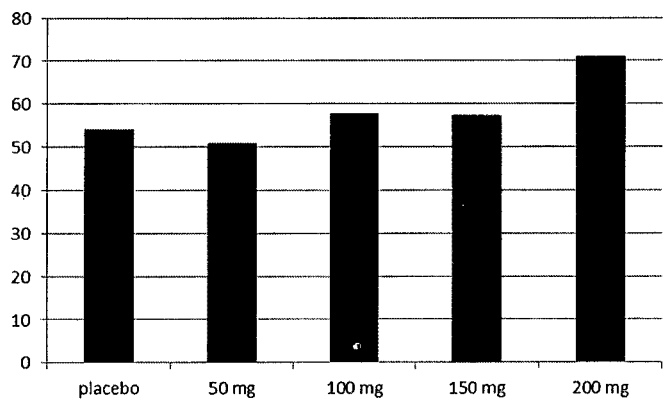
Figure 4A:
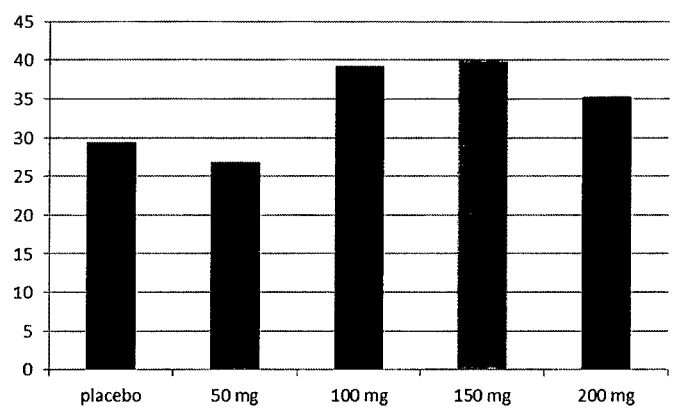
FIGS. 4A-4C are graphs depicting the percentage of patients achieving at least a 50% improvement in pain, after treatment with placebo or a monohydrochloride of Compound A, at EOT (FIG. 4A), at 2 weeks (FIG. 4B), and at 12 weeks (FIG. 4C).
Figure 4B:
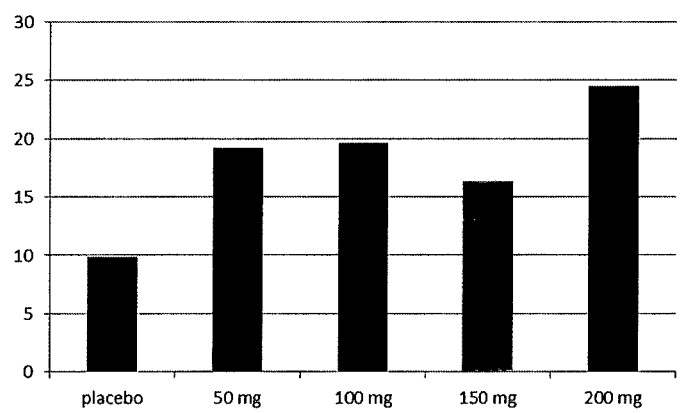
Figure 4C:
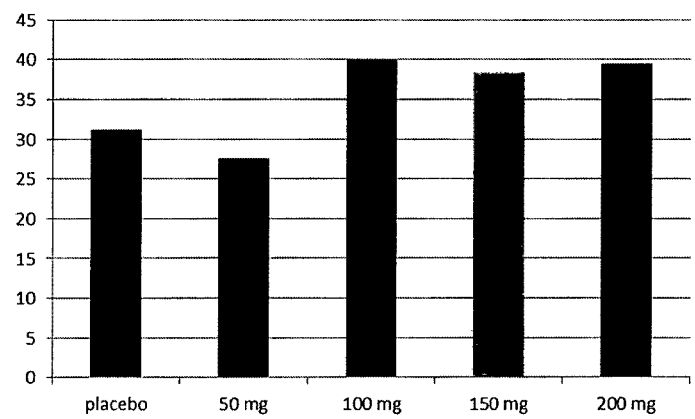
Figure 5A:
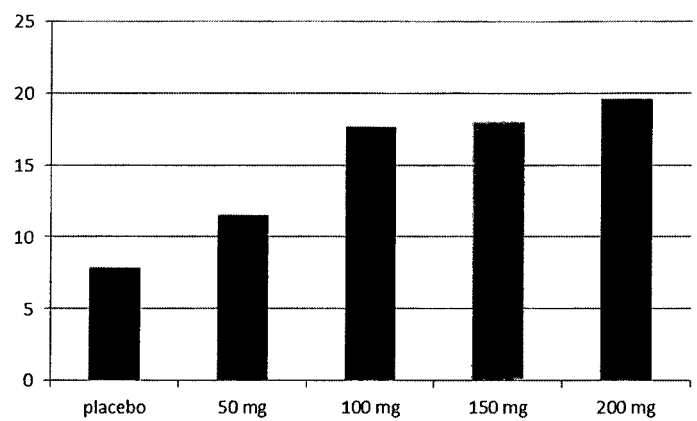
FIGS. 5A-5C are graphs depicting the percentage of patients achieving at least a 70% improvement in pain, after treatment with placebo or a monohydrochloride of Compound A, at EOT (FIG. 5A), at 2 weeks (FIG. 5B), and at 12 weeks (FIG. 5C).
Figure 5B:
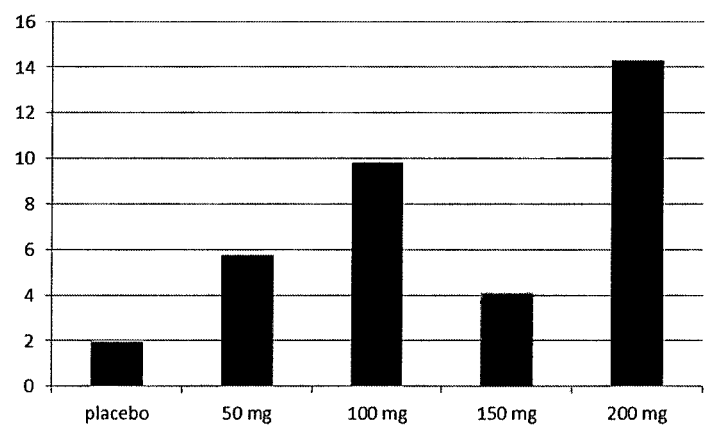
Figure 5C:
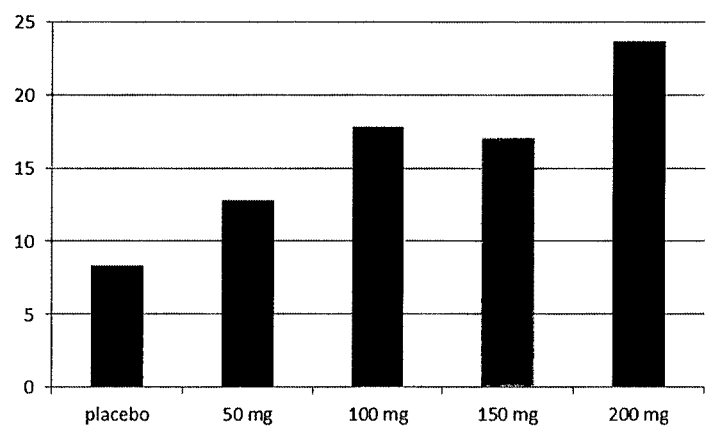

Achievement rate (percentage of subjects showing pain improvement) was also used to measure clinical improvement. The percentages of patients achieving at least a 30% improvement in pain after treatment with placebo or one of the doses of Compound A are shown in FIG. 3A (at EOT), FIG. 3B (at 2 weeks), and FIG. 3C (at 12 weeks). The percentages of patients achieving at least a 50% improvement in pain after treatment with placebo or one of the doses of Compound A are shown in FIG. 4A (at EOT), FIG. 4B (at 2 weeks), and FIG. 4C (at 12 weeks). The percentages of patients achieving at least a 70% improvement in pain after treatment with placebo or one of the doses of Compound A are shown in FIG. 5A (at EOT), FIG. 5B (at 2 weeks), and FIG. 5C (at 12 weeks).

Figure 6A:
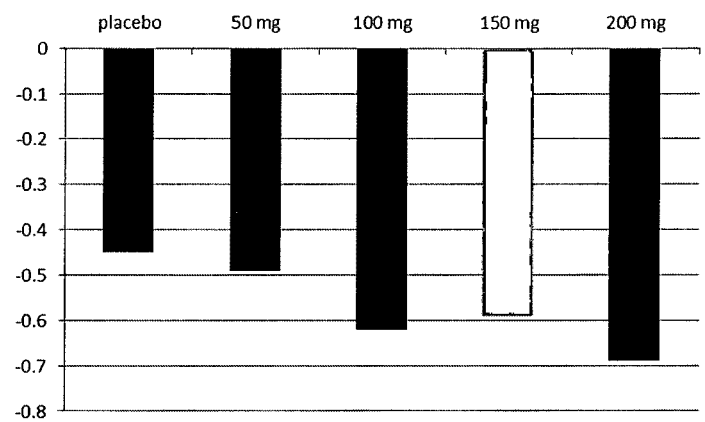
FIGS. 6A-6C are graphs depicting the amount of change from baseline in Health Assessment Questionnaire Disability Index (HAQ-DI) scores, after treatment with placebo or a monohydrochloride of Compound A, at EOT (FIG. 6A), at 2 weeks (FIG. 6B), and at 12 weeks (FIG. 6C).
Figure 6B:
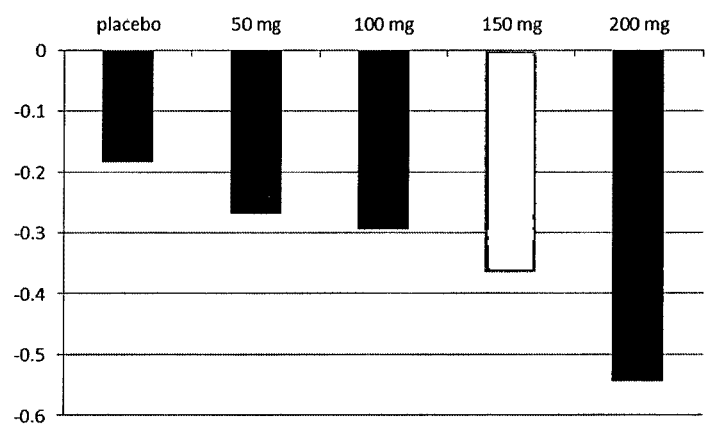
Figure 6C:
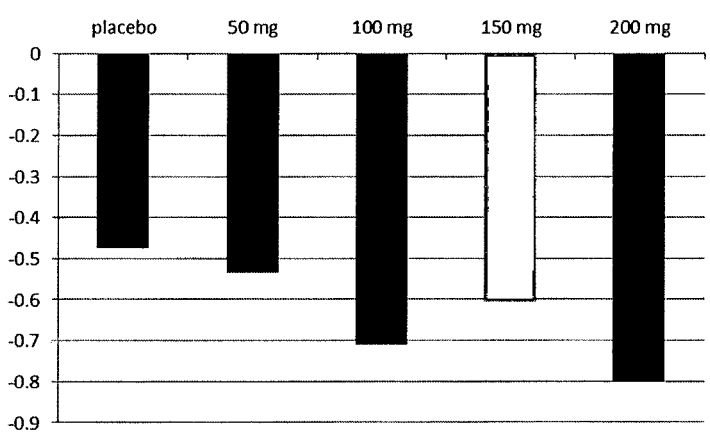

The HAQ-DI (Health Assessment Questionnaire Disability Index) questionnaire was used to assess improvement in quality of life in treated patients. The HAQ-DI assesses the extent of a subject's functional ability by assessing the degree of difficulty a subject has experienced during the past week in eight categories of daily living activities: dressing and grooming, arising, eating, walking, hygiene, reach, grip, and common daily activities. Higher HAQ-DI scores indicate worse functioning by the subject. The amounts of change from baseline in HAQ-DI scores after treatment with placebo or one of the doses of Compound A are shown in FIG. 6A (at EOT), FIG. 6B (at 2 weeks), and FIG. 6C (at 12 weeks).

Figure 7A:
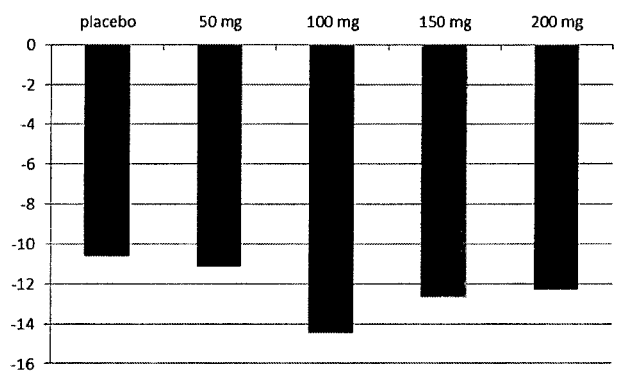
FIGS. 7A-7C are graphs depicting the amount of change from baseline in number of tender joint counts (TJC) in subjects, after treatment with placebo or a monohydrochloride of Compound A, at EOT (FIG. 7A), at 2 weeks (FIG. 7B), and at 12 weeks (FIG. 7C).
Figure 7B:
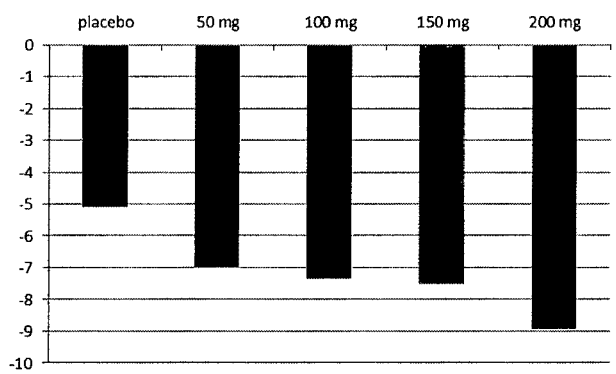
Figure 7C:
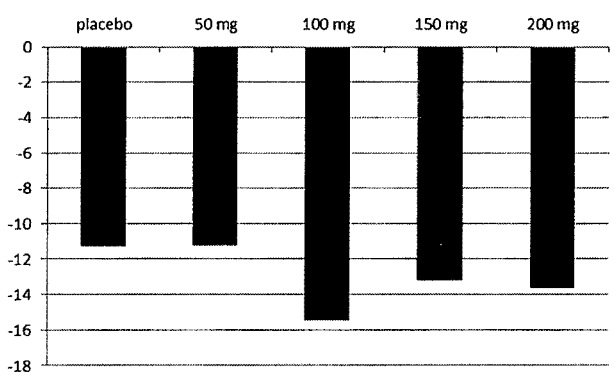

Tender Joint Count (TJC; number of joints out of 68 joints that are painful when pressed) was assessed to determine the number of joints that were considered tender or painful. The amount of change in TJC from baseline after treatment with placebo or one of the doses of Compound A is shown in FIG. 7A (at EOT), FIG. 7B (at 2 weeks), and FIG. 7C (at 12 weeks).

Figure 8A:
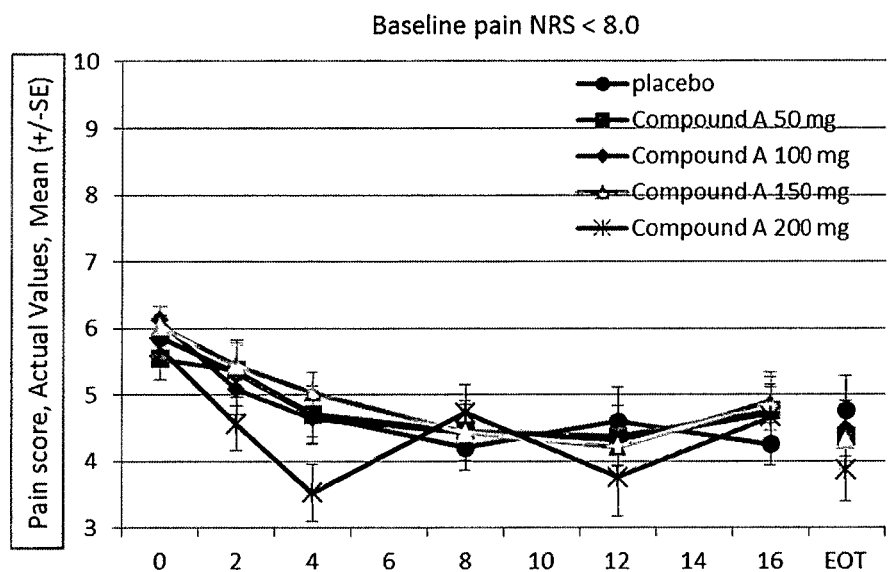
FIGS. 8A-8B are graphs depicting change from baseline in pain NRS, after treatment with placebo or a monohydrochloride of Compound A, in patients with lower baseline pain levels (FIG. 8A) or higher baseline pain levels (FIG. 8B).
Figure 8B:
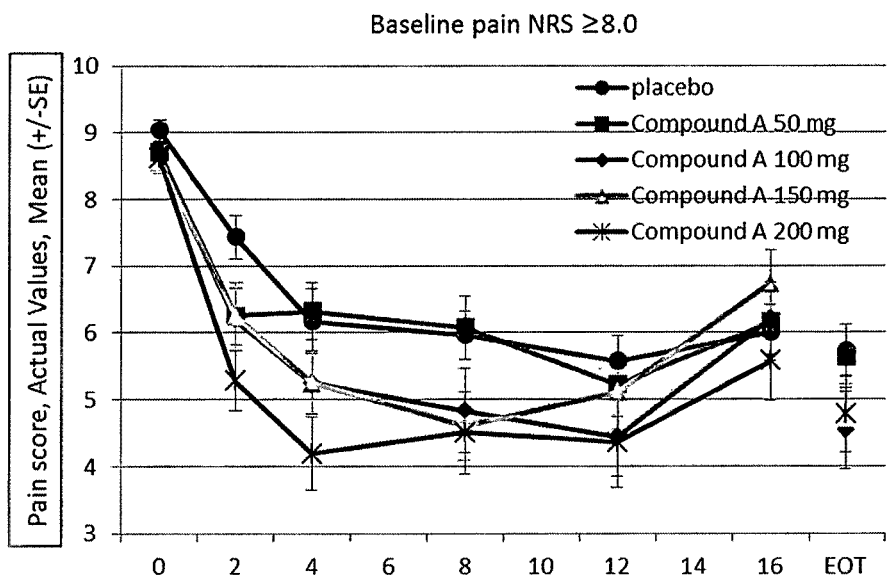

Change in pain NRS was evaluated in two subgroups of patients, those with higher baseline pain levels (median baseline pain NRS≥8.0) and those with lower baseline pain levels (median baseline pain NRS<8.0). Larger decreases in pain NRS were observed in subjects that began treatment with higher baseline pain levels. See FIGS. 8A and 8B. Although the magnitude of decrease in pain NRS was different between lower and higher baseline pain NRS subgroups, both subgroups ultimately achieved a pain NRS score of approximately 4.

The clinical study showed that rapid (within 2 weeks) and long-lasting (12 weeks) anti-pain effects were observed following treatment with Compound A. The improvement in pain scores within two weeks of treatment with Compound A indicates that the compound had an analgesic effect, as any improvement resulting solely from an anti-inflammatory effect would have required a longer period of time before showing a beneficial effect.

The incidence of serious adverse events (SAEs) and severe treatment-emergent adverse events (TEAEs) in the clinical study was low (3.4% and 2.9%, respectively) in subjects who received treatment with one of the doses of Compound A in the clinical study. Compound A was safe and tolerated at doses up to 200 mg over 12 weeks of treatment.

Example 4: Pharmacokinetic Assessments

Figure 9:
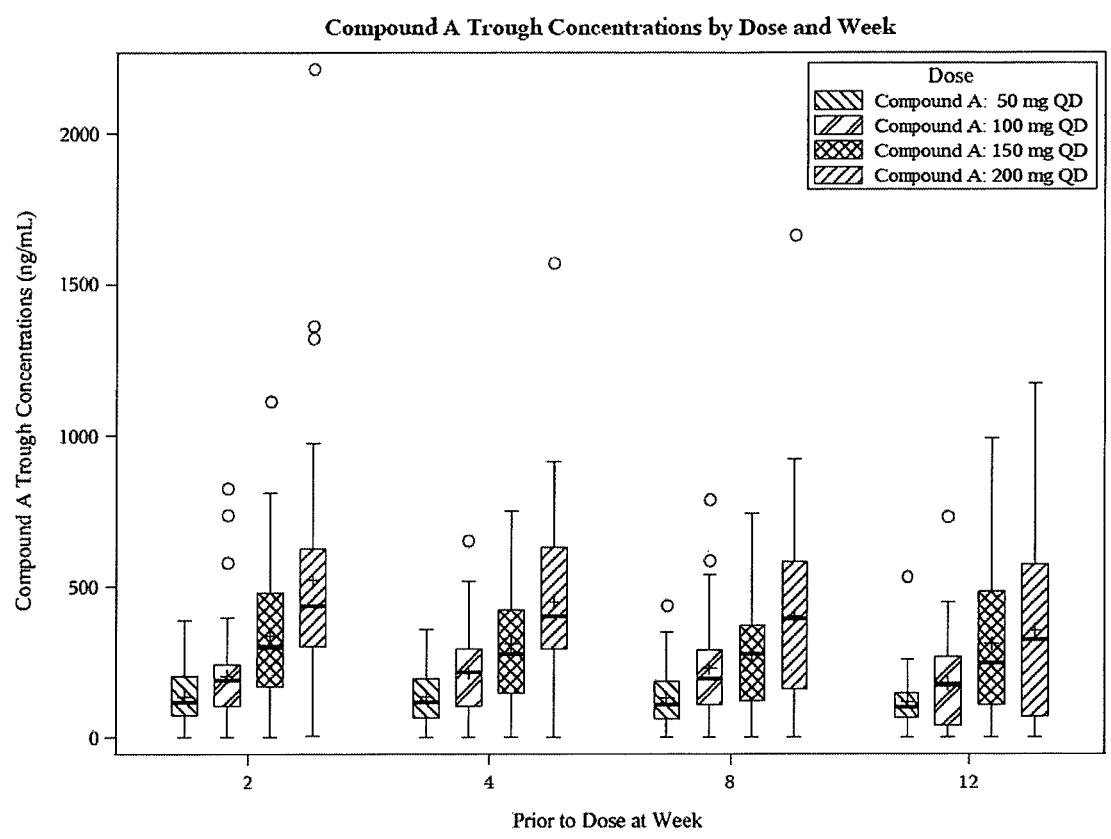
FIG. 9 is a graph depicting trough concentrations ($C_{trough}$) of Compound A in blood samples collected from patients receiving 50 mg, 100 mg, 150 mg, or 200 mg of a Compound A once daily, measured prior to dosing at weeks 2, 4, 8, and 12.

In the human clinical study described in Example 3, blood samples were collected from subjects prior to dosing at weeks 2, 4, 8, and 12 for the quantification of plasma Compound A levels. Trough concentrations ($C_{trough}$) of Compound A are shown in FIG. 9. Mean trough concentrations increased as dose increased from 50 mg to 200 mg and trough concentrations were maintained throughout the study. See Table 3.

TABLE 3

Compound A Trough Plasma Concentrations (ng/mL) by Treatment and Visit

| Statistics | Compound A 50 mg QD (N = 46) | Compound A 100 mg QD (N = 47) | Compound A 150 mg QD (N = 44) | Compound A 200 mg QD (N = 46) |
|---|---|---|---|---|
| 2 week | | | | |
| N | 46 | 46 | 41 | 46 |
| Mean (SD) | 134 (87.0) | 204 (168) | 335 (242) | 521 (381) |
| Ratio (1) | 1.00 | 1.52 | 2.51 | 3.89 |
| Median | 118 | 191 | 300 | 436 |
| Min-Max | 0.00-387 | 0.00-825 | 1.47-1110 | 5.01-2210 |
| CV % | 65.1 | 82.6 | 72.1 | 73.1 |
| 4 week | | | | |
| N | 46 | 44 | 41 | 40 |
| Mean (SD) | 135 (88.4) | 216 (144) | 309 (217) | 450 (300) |
| Ratio (1) | 1.00 | 1.60 | 2.28 | 3.33 |
| Median | 119 | 215 | 277 | 402 |
| Min-Max | 0.00-356 | 0.00-650 | 0.00-748 | 0.00-1570 |
| CV % | 65.3 | 66.5 | 70.2 | 66.6 |
| 8 week | | | | |
| N | 45 | 42 | 41 | 36 |
| Mean (SD) | 129 (102) | 228 (167) | 272 (185) | 402 (336) |
| Ratio (1) | 1.00 | 1.77 | 2.10 | 3.11 |
| Median | 108 | 194 | 277 | 392 |
| Min-Max | 0.00-436 | 0.00-785 | 0.00-743 | 0.00-1660 |
| CV % | 79.1 | 73.1 | 68.2 | 83.5 |
| 12 week | | | | |
| N | 40 | 42 | 40 | 35 |
| Mean (SD) | 119 (96.9) | 178 (156) | 312 (252) | 354 (281) |
| Ratio (1) | 1.00 | 1.50 | 2.63 | 2.98 |
| Median | 100 | 175 | 246 | 323 |
| Min-Max | 0.00-531 | 0.00-728 | 0.00-992 | 0.00-1170 |
| CV % | 81.7 | 88.0 | 80.7 | 79.4 |

Individual concentrations that were BLQ (<2.00 ng/mL) were assigned a plasma concentration of 0.
(1) Mean ratio relative to Compound A 50 mg QD at the same visit.

Figure 10A:
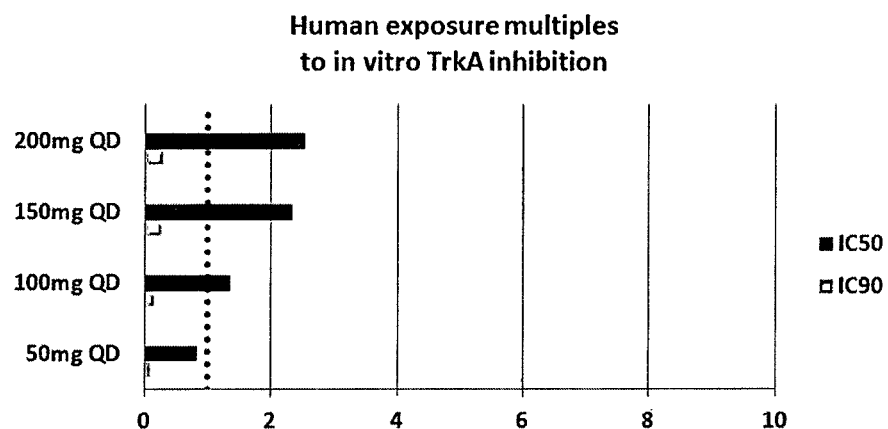
FIG. 10A-10B are graphs depicting human exposure multiples to in vitro TrkA inhibition (FIG. 10A) and human exposure multiples to inhibition of NGF-induced hyperalgesia in rats (FIG. 10B).
Figure 10B:
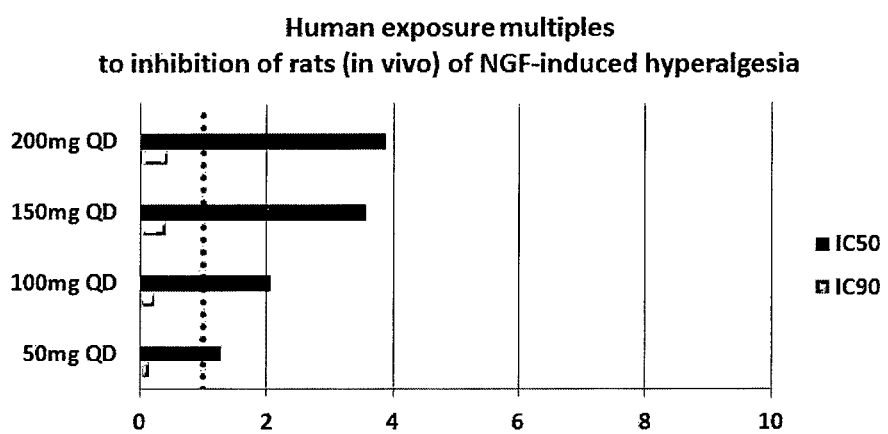

Human $C_{trough}$ multiples to preclinical pharmacology results were determined. The multiples were calculated by dividing human exposures (mean $C_{trough}$ at week 12) by preclinical $IC_{50}$ or $IC_{90}$ values. FIG. 1A shows human exposure multiples to in vitro TrkA inhibition. FIG. 10B shows human exposure multiples to inhibition of NGF-induced hyperalgesia in rats.

Example 5: Effect of Oral Administration of Compound A in a Mouse Cyclophosphamide (CYP)-Induced Cystitis Model The inhibitory effect of Compound A on lower abdominal licking time was evaluated in a mouse CYP-induced cystitis model. The evaluation was performed according to M. Fujita et al., Eur J Pain. 20 (2016) 79-91. Male C57BL/6J mice (Charles River Laboratories Japan, Inc.) were used as the experimental animals.

Once per day for four days (Days 1-4) 20 mg/mL of CYP (Sigma) dissolved in saline solution was intraperitoneally administered to a vehicle group, a Compound A administration group, and an anti-NGF antibody group at a volume of 10 mL/kg, and saline solution was intraperitoneally administered to a sham group at a volume of 10 mL/kg. A monohydrochloride of Compound A was dissolved in 0.5% methyl cellulose (MC) to prepare 3 mg/mL, 6 mg/mL, and 10 mg/mL solutions of Compound A.

Once per day for three days (Days 7-9), 0.5% (w/v) MC was orally administered to the sham group, the vehicle group, and the anti-NGF antibody group, and 3 mg/mL, 6 mg/mL, or 10 mg/mL of solutions of Compound A was orally administered to the Compound A administration group at a volume of 10 mL/kg. In addition, a single time (Day 7) isotype control BE 0083 (Bio X Cell) was intraperitoneally administered to the sham group, the vehicle group, and the Compound A administration group and monoclonal anti-Nerve Growth Factor-β (NGF) antibody (Sigma) was intraperitoneally administered to the anti-NGF antibody administration group at a volume of 150 μg per head.

Figure 11:
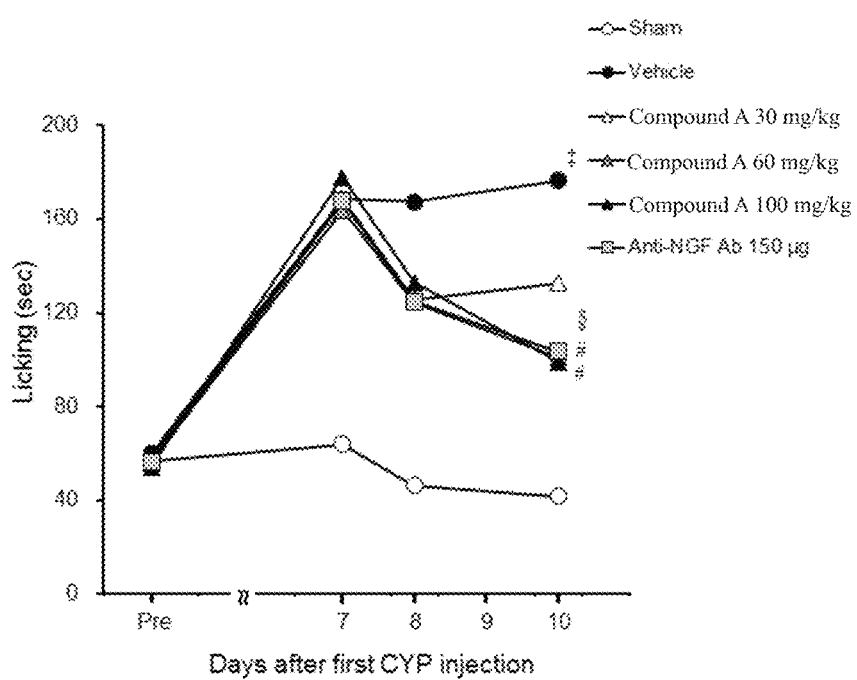
FIG. 11 shows the lower abdominal licking times for CYP-induced cystitis model mice to which a vehicle, a monohydrochloride of Compound A, or an anti-NGF antibody was administered.

The behavior of the mice was recorded for 90 minutes using a video camera prior to the initial administration of CYP (Pre) and on Day 7, Day 8, and Day 10, and the lower abdominal licking time (seconds) was measured. On Day 7 and Day 8, after recording the behavior of the mice, 0.5% (w/v) MC was orally administered to the sham group, the vehicle group, and the anti-NGF antibody group, and a solution of Compound A was orally administered to the Compound A administration group. Furthermore, on Day 7, after recording the behavior of the mice, isotype control BE0083 was intraperitoneally administered to the sham group, the vehicle group, and the Compound A administration group, and the anti-NGF antibody was intraperitoneally administered to the anti-NGF antibody administration group. The mean values of the licking times of the individual animals were calculated for each group, and the results are shown in FIG. 11. Compound A reduced lower abdominal licking time in this cystitis animal model.

Example 6: Effect of Oral Administration of Compound A on Frequent Urination in a Rat CYP-Induced Cystitis Model The effect of Compound A on frequent urination, calculated by single voided volume and intermicturition interval, was evaluated using a rat CYP-induced cystitis model. The evaluation was performed according to G M. Herrera et al., PLoS ONE 5 (8): e12298. Female CD (SD) rats (Charles River Laboratories Japan, Inc.) were used as the experimental animals. A monohydrochloride of Compound A was dissolved in 0.5% MC to prepare 2 mg/mL and 6 mg/mL solutions of Compound A.

30 mg/mL of CYP (Sigma) dissolved in saline was intraperitoneally administered in the vehicle group and Compound A group and saline was intraperitoneally administered in the sham group at 5 mL/kg (Day 1).

0.5% (w/v) MC was orally administered once a day for 2 days (Day 1-2) in the sham group and vehicle group at 5 mL/kg, and 2 mg/mL or 6 mg/mL solutions of Compound A was orally administered twice a day (Day 1-2) in the Compound A administration group at 5 mL/kg.

Figure 12A:
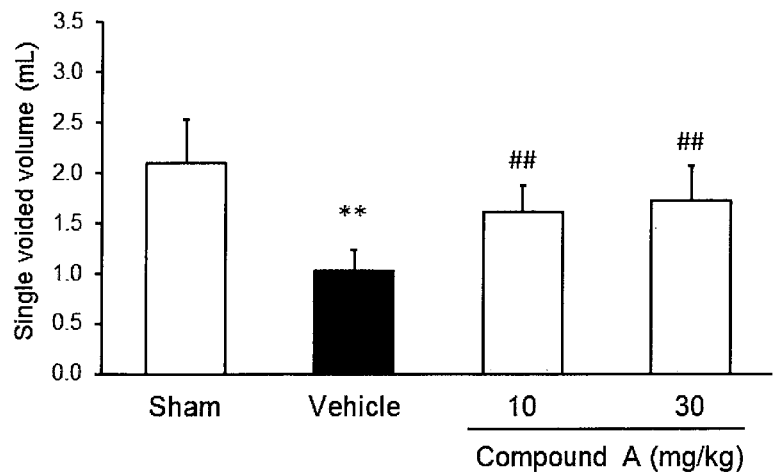
FIG. 12A shows the effect of Compound A on single-voided volume in rats with CYP-induced cystitis.
Figure 12B:
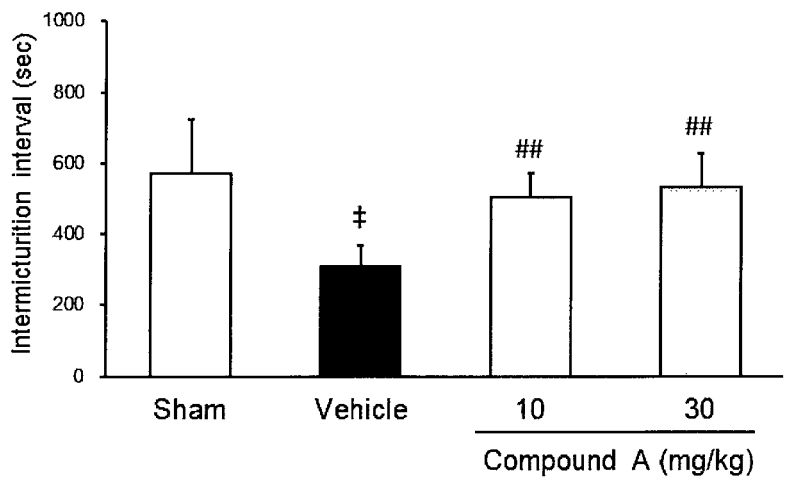
FIG. 12B shows the effect of Compound A on intermicturition interval in rats with CYP-induced cystitis.

Intravesical pressure and voided volume were measured by cystometry on Day 3, and single voided volumes and intermicturition intervals were calculated. Mean values were calculated for each group from individual single voided volumes and intermicturition intervals, and the results are shown in FIG. 12A and FIG. 12B, respectively. Compound A suppressed frequent urination in this cystitis animal model.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of treating or preventing pain in a human subject in need thereof, comprising administering to the human subject a therapeutically effective amount of a compound represented by the following chemical structural formula:

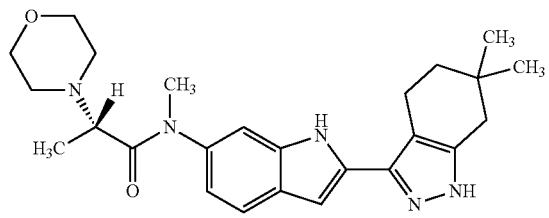 [SMILES: C[C@@H](C(=O)N(C)c1ccc2cc(-c3n[nH]c4c3CCC(C)(C)C4)[nH]c2c1)N1CCOCC1]

or a pharmaceutically acceptable salt thereof.

2. The method of claim 1, wherein the pain is neuropathic pain, nociceptive pain, or mixed pain.

3. The method of claim 1, wherein the pain is inflammatory pain, musculoskeletal pain, or cancer pain.

4. The method of claim 1, wherein the pain is pain of osteoarthritis, low back pain, pain of interstitial cystitis, or pain of diabetic peripheral neuropathy.

5. The method of claim 1, wherein the pain is pain of rheumatoid arthritis.

6. The method of claim 1, wherein the pain is not pain of rheumatoid arthritis.

7. The method of claim 1, wherein the pain is painful bladder syndrome, bladder pain syndrome, or chronic pelvic pain syndrome.

8. The method of claim 1, wherein the pain is associated with inflammation, pancreatitis, kidney stones, a headache, dysmenorrhea, musculoskeletal pain, a sprain, visceral pain, an ovarian cyst, prostatitis, cystitis, inflammatory bowel disease, post-surgical pain, a migraine, trigeminal neuralgia, burns, wounds, trauma, post-herpetic neuralgia, a musculoskeletal disease, ankylosing spondylitis, a periarticular pathology, cancer, bone metastases, HIV, myocardial infarction, fracture, gout, joints, sciatica, a sickle cell crisis, endometriosis, fibromyalgia, incisional pain, erythromelalgia, malignant melanoma, Sjogren's syndrome, asthma, chronic abacterial prostatitis, uterine fibroids, vulvodynia, phantom limb pain, root avulsions, diabetic neuropathic pain, painful traumatic mononeuropathy, painful polyneuropathy, a central pain syndrome, repetitive motion pain, myofascial pain, perioperative pain, chronic pain, angina, primary hyperalgesia, secondary hyperalgesia, primary allodynia, secondary allodynia, osteoporosis, irritable bowel syndrome, pulpitis, a contusion of the skin, tendonitis, colic, appendicitis, peptic ulcer disease, bladder distension, a bruise, peritendinitis, frozen shoulder, spinal compression fracture, spinal stricture, spinal stenosis, spinal disc herniation, cervicobranchial syndrome, spinal burst fracture, pain after exodontia, acute arterial occlusion, or erythromelalgia.

9. The method of claim 1, wherein the pain is moderate pain, moderate to severe pain, or severe pain.

10. The method of claim 1, wherein the pharmaceutically acceptable salt is a monohydrochloride.

11. The method of claim 1, wherein the compound or pharmaceutically acceptable salt thereof is administered orally.

12. The method of claim 1, wherein the compound or pharmaceutically acceptable salt thereof is administered once daily.

13. The method of claim 1, wherein the compound or pharmaceutically acceptable salt thereof is administered orally at a dose equivalent to no less than 50 mg of the compound.

14. The method of claim 13, wherein the compound or pharmaceutically acceptable salt thereof is administered orally at a dose equivalent to about 50-400 mg of the compound.

15. The method of claim 13, wherein the compound or pharmaceutically acceptable salt thereof is administered orally at a dose equivalent to about 50-200 mg of the compound.

16. The method of claim 13, wherein the compound or pharmaceutically acceptable salt thereof is administered orally at a dose equivalent to about 75-200 mg of the compound.

17. The method of claim 13, wherein the compound or pharmaceutically acceptable salt thereof is administered orally at a dose equivalent to about 75-150 mg of the compound.

18. The method of claim 13, wherein the compound or pharmaceutically acceptable salt thereof is administered orally at a dose equivalent to about 75 mg, about 100 mg, about 125 mg, or about 150 mg of the compound.

19. The method of claim 1, wherein the compound or pharmaceutically acceptable salt thereof is administered once daily and results in mean trough concentration ($C_{trough}$) of the compound of about 100 ng/mL to about 550 ng/mL for at least about 12 weeks.

20. The method of claim 19, wherein the compound or pharmaceutically acceptable salt thereof is administered once daily and results in mean trough concentration ($C_{trough}$) of the compound of about 100 ng/mL to about 150 ng/mL for at least about 12 weeks.

21. The method of claim 19, wherein the compound or pharmaceutically acceptable salt thereof is administered once daily and results in mean trough concentration ($C_{trough}$) of the compound of about 150 ng/mL to about 250 ng/mL for at least about 12 weeks.

22. The method of claim 19, wherein the compound or pharmaceutically acceptable salt thereof is administered once daily and results in mean trough concentration ($C_{trough}$) of the compound of about 250 ng/mL to about 350 ng/mL for at least about 12 weeks.

23. The method of claim 19, wherein the compound or pharmaceutically acceptable salt thereof is administered once daily and results in mean trough concentration ($C_{trough}$) of the compound of about 300 ng/mL to about 550 ng/mL for at least about 12 weeks.

24. A method of treating or preventing interstitial cystitis in a human subject in need thereof, comprising administering to the human subject a therapeutically effective amount of a compound represented by the following chemical structural formula:

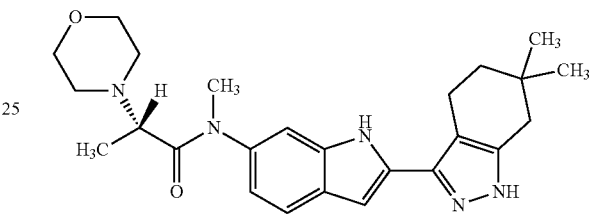

or a pharmaceutically acceptable salt thereof.

25. The method of claim 24, wherein the interstitial cystitis is characterized by at least one symptom selected from the group consisting of frequent urination, nocturia, urinary urgency, increased desire to urinate, hypersensitive bladder, bladder discomfort, bladder pain, and inflammation of the bladder.

26. The method of claim 24, wherein the interstitial cystitis is Hunner-type interstitial cystitis or non-Hunner-type interstitial cystitis.

27. The method of claim 24, wherein the pharmaceutically acceptable salt is a monohydrochloride.

28. The method of claim 24, wherein the compound or pharmaceutically acceptable salt thereof is administered orally.

29. The method of claim 24, wherein the compound or pharmaceutically acceptable salt thereof is administered once daily.

30. A method of treating pain in a human subject in need thereof, comprising administering to the human subject a therapeutically effective amount of a compound represented by the following chemical structural formula:

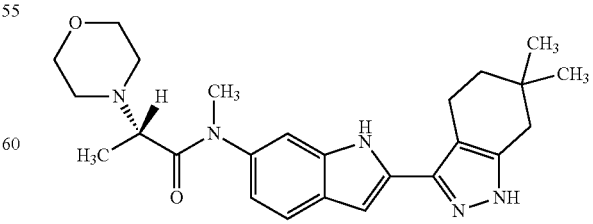

or a pharmaceutically acceptable salt thereof.

31. The method of claim 30, wherein the pain is moderate pain, moderate to severe pain, or severe pain.

32. The method of claim 30, wherein the pharmaceutically acceptable salt is a monohydrochloride.

33. The method of claim 30, wherein the compound or pharmaceutically acceptable salt thereof is administered orally.

34. The method of claim 30, wherein the compound or pharmaceutically acceptable salt thereof is administered once daily.

35. The method of claim 30, wherein the compound or pharmaceutically acceptable salt thereof is administered orally at a dose equivalent to no less than 50 mg of the compound.

36. The method of claim 35, wherein the compound or pharmaceutically acceptable salt thereof is administered orally at a dose equivalent to about 50-200 mg of the compound.

37. The method of claim 35, wherein the compound or pharmaceutically acceptable salt thereof is administered orally at a dose equivalent to about 50 mg of the compound.

38. The method of claim 35, wherein the compound or pharmaceutically acceptable salt thereof is administered orally at a dose equivalent to about 100 mg of the compound.

39. The method of claim 35, wherein the compound or pharmaceutically acceptable salt thereof is administered orally at a dose equivalent to about 150 mg of the compound.

40. The method of claim 30, wherein the compound or pharmaceutically acceptable salt thereof is administered once daily and results in mean trough concentration ($C_{trough}$) of the compound of about 100 ng/mL to about 550 ng/mL for at least about 12 weeks.

41. The method of claim 40, wherein the compound or pharmaceutically acceptable salt thereof is administered once daily and results in mean trough concentration ($C_{trough}$) of the compound of about 150 ng/mL to about 250 ng/mL for at least about 12 weeks.

42. The method of claim 40, wherein the compound or pharmaceutically acceptable salt thereof is administered once daily and results in mean trough concentration ($C_{trough}$) of the compound of about 250 ng/mL to about 350 ng/mL for at least about 12 weeks.

43. The method of claim 30, wherein the pain is pain of interstitial cystitis.

44. The method of claim 43, wherein the pain is moderate pain, moderate to severe pain, or severe pain.

45. The method of claim 43, wherein the pharmaceutically acceptable salt is a monohydrochloride.

46. The method of claim 43, wherein the compound or pharmaceutically acceptable salt thereof is administered orally.

47. The method of claim 43, wherein the compound or pharmaceutically acceptable salt thereof is administered once daily.

48. The method of claim 43, wherein the compound or pharmaceutically acceptable salt thereof is administered orally at a dose equivalent to no less than 50 mg of the compound.

49. The method of claim 48, wherein the compound or pharmaceutically acceptable salt thereof is administered orally at a dose equivalent to about 50-200 mg of the compound.

50. The method of claim 48, wherein the compound or pharmaceutically acceptable salt thereof is administered orally at a dose equivalent to about 50 mg of the compound.

51. The method of claim 48, wherein the compound or pharmaceutically acceptable salt thereof is administered orally at a dose equivalent to about 100 mg of the compound.

52. The method of claim 48, wherein the compound or pharmaceutically acceptable salt thereof is administered orally at a dose equivalent to about 150 mg of the compound.

53. The method of claim 43, wherein the compound or pharmaceutically acceptable salt thereof is administered once daily and results in mean trough concentration ($C_{trough}$) of the compound of about 100 ng/mL to about 550 ng/mL for at least about 12 weeks.

54. The method of claim 43, wherein the compound or pharmaceutically acceptable salt thereof is administered once daily and results in mean trough concentration ($C_{trough}$) of the compound of about 150 ng/mL to about 250 ng/mL for at least about 12 weeks.

55. The method of claim 43, wherein the compound or pharmaceutically acceptable salt thereof is administered once daily and results in mean trough concentration ($C_{trough}$) of the compound of about 250 ng/mL to about 350 ng/mL for at least about 12 weeks.

56. The method of claim 30, wherein the pain is painful bladder syndrome.

57. The method of claim 56, wherein the pain is moderate pain, moderate to severe pain, or severe pain.

58. The method of claim 56, wherein the pharmaceutically acceptable salt is a monohydrochloride.

59. The method of claim 56, wherein the compound or pharmaceutically acceptable salt thereof is administered orally.

60. The method of claim 56, wherein the compound or pharmaceutically acceptable salt thereof is administered once daily.

61. The method of claim 56, wherein the compound or pharmaceutically acceptable salt thereof is administered orally at a dose equivalent to no less than 50 mg of the compound.

62. The method of claim 61, wherein the compound or pharmaceutically acceptable salt thereof is administered orally at a dose equivalent to about 50-200 mg of the compound.

63. The method of claim 61, wherein the compound or pharmaceutically acceptable salt thereof is administered orally at a dose equivalent to about 50 mg of the compound.

64. The method of claim 61, wherein the compound or pharmaceutically acceptable salt thereof is administered orally at a dose equivalent to about 100 mg of the compound.

65. The method of claim 61, wherein the compound or pharmaceutically acceptable salt thereof is administered orally at a dose equivalent to about 150 mg of the compound.

66. The method of claim 56, wherein the compound or pharmaceutically acceptable salt thereof is administered once daily and results in mean trough concentration ($C_{trough}$) of the compound of about 100 ng/mL to about 550 ng/mL for at least about 12 weeks.

67. The method of claim 66, wherein the compound or pharmaceutically acceptable salt thereof is administered once daily and results in mean trough concentration ($C_{trough}$) of the compound of about 150 ng/mL to about 250 ng/mL for at least about 12 weeks.

68. The method of claim 66, wherein the compound or pharmaceutically acceptable salt thereof is administered once daily and results in mean trough concentration ($C_{trough}$) of the compound of about 250 ng/mL to about 350 ng/mL for at least about 12 weeks.

69. The method of claim 30, wherein the pain is bladder pain syndrome.

70. The method of claim 69, wherein the pain is moderate pain, moderate to severe pain, or severe pain.

71. The method of claim 69, wherein the pharmaceutically acceptable salt is a monohydrochloride.

72. The method of claim 69, wherein the compound or pharmaceutically acceptable salt thereof is administered orally.

73. The method of claim 69, wherein the compound or pharmaceutically acceptable salt thereof is administered once daily.

74. The method of claim 69, wherein the compound or pharmaceutically acceptable salt thereof is administered orally at a dose equivalent to no less than 50 mg of the compound.

75. The method of claim 74, wherein the compound or pharmaceutically acceptable salt thereof is administered orally at a dose equivalent to about 50-200 mg of the compound.

76. The method of claim 74, wherein the compound or pharmaceutically acceptable salt thereof is administered orally at a dose equivalent to about 50 mg of the compound.

77. The method of claim 74, wherein the compound or pharmaceutically acceptable salt thereof is administered orally at a dose equivalent to about 100 mg of the compound.

78. The method of claim 74, wherein the compound or pharmaceutically acceptable salt thereof is administered orally at a dose equivalent to about 150 mg of the compound.

79. The method of claim 69, wherein the compound or pharmaceutically acceptable salt thereof is administered once daily and results in mean trough concentration ($C_{trough}$) of the compound of about 100 ng/mL to about 550 ng/mL for at least about 12 weeks.

80. The method of claim 79, wherein the compound or pharmaceutically acceptable salt thereof is administered once daily and results in mean trough concentration ($C_{trough}$) of the compound of about 150 ng/mL to about 250 ng/mL for at least about 12 weeks.

81. The method of claim 79, wherein the compound or pharmaceutically acceptable salt thereof is administered once daily and results in mean trough concentration ($C_{trough}$) of the compound of about 250 ng/mL to about 350 ng/mL for at least about 12 weeks.

82. The method of claim 30, wherein the pain is chronic pelvic pain syndrome.

83. The method of claim 82, wherein the pain is moderate pain, moderate to severe pain, or severe pain.

84. The method of claim 82, wherein the pharmaceutically acceptable salt is a monohydrochloride.

85. The method of claim 82, wherein the compound or pharmaceutically acceptable salt thereof is administered orally.

86. The method of claim 82, wherein the compound or pharmaceutically acceptable salt thereof is administered once daily.

87. The method of claim 82, wherein the compound or pharmaceutically acceptable salt thereof is administered orally at a dose equivalent to no less than 50 mg of the compound.

88. The method of claim 87, wherein the compound or pharmaceutically acceptable salt thereof is administered orally at a dose equivalent to about 50-200 mg of the compound.

89. The method of claim 87, wherein the compound or pharmaceutically acceptable salt thereof is administered orally at a dose equivalent to about 50 mg of the compound.

90. The method of claim 87, wherein the compound or pharmaceutically acceptable salt thereof is administered orally at a dose equivalent to about 100 mg of the compound.

91. The method of claim 87, wherein the compound or pharmaceutically acceptable salt thereof is administered orally at a dose equivalent to about 150 mg of the compound.

92. The method of claim 82, wherein the compound or pharmaceutically acceptable salt thereof is administered once daily and results in mean trough concentration ($C_{trough}$) of the compound of about 100 ng/mL to about 550 ng/mL for at least about 12 weeks.

93. The method of claim 92, wherein the compound or pharmaceutically acceptable salt thereof is administered once daily and results in mean trough concentration ($C_{trough}$) of the compound of about 150 ng/mL to about 250 ng/mL for at least about 12 weeks.

94. The method of claim 92, wherein the compound or pharmaceutically acceptable salt thereof is administered once daily and results in mean trough concentration ($C_{trough}$) of the compound of about 250 ng/mL to about 350 ng/mL for at least about 12 weeks.

95. A method of treating interstitial cystitis in a human subject in need thereof, comprising administering to the human subject a therapeutically effective amount of a compound represented by the following chemical structural formula:

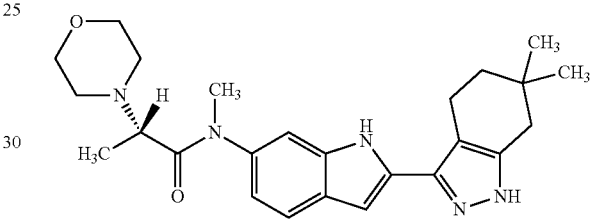

or a pharmaceutically acceptable salt thereof.

96. The method of claim 95, wherein the interstitial cystitis is characterized by at least one symptom selected from the group consisting of frequent urination, nocturia, urinary urgency, increased desire to urinate, hypersensitive bladder, bladder discomfort, bladder pain, and inflammation of the bladder.

97. The method of claim 95, wherein the interstitial cystitis is Hunner-type interstitial cystitis.

98. The method of claim 95, wherein the interstitial cystitis is non-Hunner-type interstitial cystitis.

99. The method of claim 95, wherein the pharmaceutically acceptable salt is a monohydrochloride.

100. The method of claim 95, wherein the compound or pharmaceutically acceptable salt thereof is administered orally.

101. The method of claim 95, wherein the compound or pharmaceutically acceptable salt thereof is administered once daily.

102. The method of claim 95, wherein the compound or pharmaceutically acceptable salt thereof is administered orally at a dose equivalent to no less than 50 mg of the compound.

103. The method of claim 102, wherein the compound or pharmaceutically acceptable salt thereof is administered orally at a dose equivalent to about 50-200 mg of the compound.

104. The method of claim 102, wherein the compound or pharmaceutically acceptable salt thereof is administered orally at a dose equivalent to about 50 mg of the compound.

105. The method of claim 102, wherein the compound or pharmaceutically acceptable salt thereof is administered orally at a dose equivalent to about 100 mg of the compound.

106. The method of claim 102, wherein the compound or pharmaceutically acceptable salt thereof is administered orally at a dose equivalent to about 150 mg of the compound.

107. The method of claim 95, wherein the compound or pharmaceutically acceptable salt thereof is administered once daily and results in mean trough concentration ($C_{trough}$) of the compound of about 100 ng/mL to about 550 ng/mL for at least about 12 weeks.

108. The method of claim 107, wherein the compound or pharmaceutically acceptable salt thereof is administered once daily and results in mean trough concentration ($C_{trough}$) of the compound of about 150 ng/mL to about 250 ng/mL for at least about 12 weeks.

109. The method of claim 107, wherein the compound or pharmaceutically acceptable salt thereof is administered once daily and results in mean trough concentration ($C_{trough}$) of the compound of about 250 ng/mL to about 350 ng/mL for at least about 12 weeks.

110. The method of claim 95, wherein the interstitial cystitis is characterized by at least one symptom selected from the group consisting of frequent urination, bladder discomfort, and bladder pain.

111. The method of claim 110, wherein the pharmaceutically acceptable salt is a monohydrochloride.

112. The method of claim 110, wherein the compound or pharmaceutically acceptable salt thereof is administered orally.

113. The method of claim 110, wherein the compound or pharmaceutically acceptable salt thereof is administered once daily.

114. The method of claim 110, wherein the compound or pharmaceutically acceptable salt thereof is administered orally at a dose equivalent to no less than 50 mg of the compound.

115. The method of claim 114, wherein the compound or pharmaceutically acceptable salt thereof is administered orally at a dose equivalent to about 50-200 mg of the compound.

116. The method of claim 114, wherein the compound or pharmaceutically acceptable salt thereof is administered orally at a dose equivalent to about 50 mg of the compound.

117. The method of claim 114, wherein the compound or pharmaceutically acceptable salt thereof is administered orally at a dose equivalent to about 100 mg of the compound.

118. The method of claim 114, wherein the compound or pharmaceutically acceptable salt thereof is administered orally at a dose equivalent to about 150 mg of the compound.

119. The method of claim 110, wherein the compound or pharmaceutically acceptable salt thereof is administered once daily and results in mean trough concentration ($C_{trough}$) of the compound of about 100 ng/mL to about 550 ng/mL for at least about 12 weeks.

120. The method of claim 119, wherein the compound or pharmaceutically acceptable salt thereof is administered once daily and results in mean trough concentration ($C_{trough}$) of the compound of about 150 ng/mL to about 250 ng/mL for at least about 12 weeks.

121. The method of claim 119, wherein the compound or pharmaceutically acceptable salt thereof is administered once daily and results in mean trough concentration ($C_{trough}$) of the compound of about 250 ng/mL to about 350 ng/mL for at least about 12 weeks.

* * * * *

UNITED STATES PATENT AND TRADEMARK OFFICE
CERTIFICATE OF CORRECTION

PATENT NO. : 11,464,782 B2
APPLICATION NO. : 17/056936
DATED : October 11, 2022
INVENTOR(S) : Yoshifumi Ueda et al.

It is certified that error appears in the above-identified patent and that said Letters Patent is hereby corrected as shown below:

On the Title page

Column 2, item (57), ABSTRACT
Line 3, delete "tetrahydro-H-indazol-3-yl" and insert -- tetrahydro-1H-indazol-3-yl --.

In the Specification

Column 3
Line 14, delete "cervicobranchial" and insert -- cervicobrachial --.

In the Claims

Column 23
Claim 8, Line 20, delete "cervicobranchial" and insert -- cervicobrachial --.

Signed and Sealed this
Twenty-eighth Day of February, 2023

Katherine Kelly Vidal
*Director of the United States Patent and Trademark Office*